(12) United States Patent
Seibold et al.

(10) Patent No.: US 12,153,055 B2
(45) Date of Patent: Nov. 26, 2024

(54) METHODS OF DETECTING AND TREATING AIRWAY INFLAMMATORY DISEASES

(71) Applicant: NATIONAL JEWISH HEALTH, Denver, CO (US)

(72) Inventors: Max Seibold, Denver, CO (US); Jamie Everman, Morrison, CO (US)

(73) Assignee: National Jewish Health, Denver, CO (US)

( * ) Notice: Subject to any disclaimer, the term of this patent is extended or adjusted under 35 U.S.C. 154(b) by 272 days.

(21) Appl. No.: 17/173,967

(22) Filed: Feb. 11, 2021

(65) Prior Publication Data

US 2021/0333289 A1 Oct. 28, 2021

Related U.S. Application Data

(63) Continuation of application No. 16/079,211, filed as application No. PCT/US2017/019452 on Feb. 24, 2017, now abandoned.

(60) Provisional application No. 62/300,633, filed on Feb. 26, 2016.

(51) Int. Cl.
*G01N 33/68* (2006.01)
*C12N 5/071* (2010.01)

(52) U.S. Cl.
CPC ....... *G01N 33/6893* (2013.01); *C12N 5/0688* (2013.01); *G01N 2800/122* (2013.01)

(58) Field of Classification Search
CPC .................. G01N 33/6893; G01N 2800/122
See application file for complete search history.

(56) References Cited

U.S. PATENT DOCUMENTS

| | | | |
|---|---|---|---|
| 2005/0208496 A1 | 9/2005 | Ohtani et al. | |
| 2011/0123530 A1* | 5/2011 | Arron | A61P 11/06 435/6.12 |
| 2019/0064185 A1 | 2/2019 | Seibold et al. | |

OTHER PUBLICATIONS

Levine et al. The role of Th2 immune pathway modulation in the treatment of severe asthma and its phenotypes: Are we getting closer? Ann Intern Med. Feb. 16, 2010; 152(4): 232-237 (Year: 2010).*

(Continued)

*Primary Examiner* — Vanessa L. Ford
*Assistant Examiner* — Sandra Carter
(74) *Attorney, Agent, or Firm* — Sheridan Ross P.C.

(57) ABSTRACT

The present invention is related to novel methods for identifying and/or diagnosing and/or treating a population of subjects that are at risk for developing and/or have an inflammatory disease of the airways, including type 2 cytokine-driven airway inflammation.

12 Claims, 12 Drawing Sheets

(56) References Cited

OTHER PUBLICATIONS

Holgate, S.T. (2013), Stratification of asthma and its treatment. Br J Clin Pharmacol, 76: 277-291 (Year: 2013).*
Idzko et al. Local application of FTY720 to the lung abrogates experimental asthma by altering dendritic cell function. J Clin Invest. Nov. 1, 2006; 116(11): 2935-2944). (Year: 2006).*
Camateros et al. "Modulation of the allergic asthma transcriptome following resiquimod treatment," Physiological Genomics, Aug. 2009, vol. 38, No. 3, pp. 303-318.
Follettie et al. "Gene expression analysis in a murine model of allergic asthma reveals overlapping disease and therapy dependent pathways in the lung," The Pharmacogenomics Journal, Mar. 2006, vol. 6, No. 2, pp. 141-152.
Izuhara "The Role of Interleukin-4 and Interleukin-13 in the Non-Immunologic Aspects of Asthma Pathogenesis," Clin Chem Lab Med, 2003, vol. 41, No. 7, pp. 860-864.
Hupin et al. "Downregulation of polymeric immunoglobulin receptor and secretory IgA antibodies in eosinophilic upper airway diseases," European Journal of Allergy and Clinical Immunology, 2013, vol. 68, No. 12, pp. 1589-1597.
Kerr et al. "Interlectin-1 Is a Prominent Protein Constituent of Pathologic Mucus Associated with Eosinophilic Airway Inflammation is Asthma," American Journal of Respiratory and Critical Care Medicine, Apr. 2014, vol. 189, No. 8, pp. 1005-1007.
Kohyama et al. "Relevance of measurement of serum periostin for diagnosing bronchial asthma and estimating its lung function abnormalities," European Respiratory Journal, Sep. 2012, vol. 40, Suppl. 56, Pub. No. 2314, Abstract No. 3280, 2 pages.
Lang et al. "Searching the Evolutionary Origin of Epithelial Mucus Protein Components—Mucins and FCGBP," Molecular Biology and Evolution, Aug. 2016, vol. 33, No. 8, pp. 1921-1936.
Lewis et al. "Unique and overlapping gene expression patterns driven by IL-4 and IL-13 in the mouse lung," The Journal of Allergy and Clinical Immunology, Apr. 2009, vol. 123, No. 4, pp. 795-804.
Louten et al. Biomarkers of Disease and Treatment in Murine and Cynomolgus Models of Chronic Asthma, Biomarker Insights, 2012, vol. 7, pp. 87-104.
Woodruff et al. "Genome-wide profiling identifies epithelial cell genes associated with asthma and with treatment response to corticosteroids," PNAS, Oct. 2007, vol. 104, No. 40, pp. 15858-15863.
Yuksel et al. "Predictive Value of Systemic and Local Lung Damage Markers for Severity and Recurrence of Wheezing In Children With Acute Bronchiolitis," American Journal of Respiratory and Critical Care Medicine, 2012, Suppl., Meeting Abstracts 185, 3 pages.
Zhen et al. "IL-13 and Epidermal Growth Factor Receptor Have Critical but Distinct Roles in Epithelial Cell Mucin Production," American Journal of Respiratory Cell and Molecular Biology, Feb. 2007, vol. 36, No. 2, pp. 244-253.
International Search Report and Written Opinion for International (PCT) Patent Application No. PCT/US2017/019452, dated May 16, 2017 13 pages.
International Preliminary Report on Patentability for International (PCT) Patent Application No. PCT/US2017/019452, dated Sep. 7, 2018 9 pages.

* cited by examiner

\* All p-values <0.05

METHODS OF DETECTING AND TREATING AIRWAY INFLAMMATORY DISEASES

CROSS-REFERENCE TO RELATED APPLICATIONS

This application is a continuation of U.S. patent application Ser. No. 16/079,211, filed Aug. 23, 2018, now abandoned, which is a national stage application under 35 U.S.C. 371 of PCT Application No. PCT/US2017/019452, having an international filing date of Feb. 24, 2017, which designated the United States, which claims the benefit of priority under 35 U.S.C. § 119(e) to U.S. Provisional Patent Application No. 62/300,633, filed Feb. 26, 2016. The entire disclosures of U.S. patent application Ser. No. 16/079,211, PCT Application No. PCT/US2017/019452 and U.S. Provisional Patent Application No. 62/300,633 are incorporated herein by reference.

FIELD OF THE INVENTION

The present invention is directed toward identifying and/or diagnosing and/or treating a population of subjects that are at risk for developing and/or have an inflammatory disease of the airways, including type 2 cytokine-driven airway inflammation (also referred to herein as a type-2 (Th2) airway inflammatory disease and/or a Th2-high airway inflammatory disease), such as type-2 high asthmatics (Th2-high asthmatic).

BACKGROUND OF THE INVENTION

Airway endotyping studies have revealed significant heterogeneity among asthmatic subjects. Most notably, it has been observed that 50% of asthmatics exhibit excessive Th2 inflammation in their bronchial airways. The Th2-high endotype has been strongly associated with a more allergic phenotype and response to corticosteroids. The inventors have previously found that expression of Th2-high asthma genes strongly correlate with IL-13 airway expression levels, implicating this cytokine in Th2 inflammation in the airway. Unfortunately, the use of Th2 endotyping has been limited by the need for airway tissue to perform the endotyping. Additionally, difficulty in measuring IL-13 in serum has prevented a plasma IL-13 assay from being used. Some surrogate Th2 markers exist; for example, upon IL-13 stimulation, periostin protein is secreted basolaterally from the polarized airway epithelium giving it access to capillaries and the general blood stream. Periostin has been used with some success in clinical trials evaluating experimental Th2 pathway inhibitor drugs. However, periostin is produced by other tissues (e.g. bone) and secreted into the blood, thereby decreasing its specificity as a marker of airway inflammation. While considerable progress in translating these and other biomarkers to the blood has been made, there is still an imperative need for additional biomarkers, specifically for Th2 inflammation. As disclosed herein, the inventors have found specific biomarkers (proteins and small molecules) that enter the blood stream only from the lung thus allowing this type of Th2 airway inflammation biomarker to be detected via a simple, blood-based clinical test.

SUMMARY OF INVENTION

One embodiment of the invention relates to a method of identifying a subject having or at risk of having a type-2 (Th2) airway inflammatory disease, the method comprising: (a) obtaining a blood sample from the subject; (b) determining the level of one or more interleukin-13 (IL-13) induced proteins in the sample; and (c) comparing the level of the one or more IL-13 induced proteins in the sample to a control sample wherein the presence and/or higher level of the one or more IL-13 induced proteins as compared to the control sample identifies the subject as having or at risk of having a type-2 airway inflammatory disease.

In another embodiment, the invention relates to a method of diagnosing and treating a type-2 (Th2) airway inflammatory disease, the method comprising: (a) obtaining a blood sample from the subject; (b) determining the level of one or more IL-13 induced proteins in the sample; (c) comparing the level of the one or more IL-13 induced proteins in the sample to a control sample, wherein the presence and/or a higher level of the one or more IL-13 induced proteins as compared to the control sample identifies the subject as having a type-2 airway inflammatory disease; and (d) administering an effective amount of an inhaled corticosteroid and/or Th2 pathway inhibitor.

In another embodiment, the invention relates to a method to endotype a subject as having Th2-high asthma, the method comprising: (a) obtaining a blood sample from the subject; (b) determining the level of one or more IL-13 induced proteins in the sample; and (c) comparing the level of the one or more IL-13 induced proteins in the sample to a control sample wherein the presence and/or higher level of the one or more IL-13 induced proteins as compared to the control sample identifies the subject as having Th2-high asthma.

In another embodiment, the invention relates to a method to predict the response of a subject to treatment with a Th2 pathway inhibitor, who has, or who is at risk of developing a Th2 airway inflammatory disease, the method comprising: (a) obtaining a blood sample from the subject; (b) determining the level of one or more interleukin-13 (IL-13) induced proteins in the sample; and (c) comparing the level of the one or more IL-13 induced proteins in the sample to a control sample wherein the presence and/or higher level of the one or more IL-13 induced proteins as compared to the control sample identifies the subject as having or at risk of having a Th2 airway inflammatory disease responsive to treatment with a Th2 path way inhibitor.

In another embodiment, the invention relates to a Th2 pathway inhibitor for use in the treatment of a Th2 airway inflammatory disease in a subject, comprising analyzing a blood sample from the subject; determining if the subject has the presence and/or a higher level of one or more IL-13 induced proteins as compared to a control level; and administering an effective amount of a Th2 pathway inhibitor to the subject if the subject has one more IL-13 induced proteins and/or one or higher levels of one or more IL-13 induced proteins.

In another embodiment, the invention relates to a method to detect one or more IL-13 induced proteins and/or small molecules in a sample from a subject comprising: (a) culturing airway epithelial cells obtained from the subject; (h) differentiating the cells at air-liquid interface (ALI); (c) treating cells with either bovine serum albumin (BSA) or IL-13 daily; (d) washing the treated cells; and C, detecting IL-13 induced proteins and/or small molecules by mass spectrometry.

In another embodiment, the invention relates to a Th2 pathway inhibitor for use in the treatment of a Th2 airway inflammatory disease.

In any of the methods or uses described herein, the type-2 airway inflammatory disease is Th2-high asthma.

In any of the methods or uses described herein, the level of the one more IL-13 induced proteins is determined by a method selected from the group consisting of mass spectrometry, Western Blotting, Elisa and PCR.

In any of the methods or uses described herein, the blood sample is a plasma sample.

In any of the methods or uses described herein, the one or more IL-13 induced proteins is selected from the group consisting of IgG Fc-receptor binding protein (FCGBP), arachidonate 15-lipoxygenase (ALOX15), plasminogen activator inhibitor 2 (PAI 2), carbonic anhydrase 2 (CA2), cystatin CN (CST1), periostin (POSTN), lysozyme C (LYZ), intelectin-1 (ITLN1), calcium-activated chloride channel 1 (CLCA 1), intelectin-2 (ITLN2), cystatin A (CSTA), mesothelin (MLN), ST6 beta-galactosamide alpha-2,6-sialyltransferase 1 (SIAT1), mucin 5AC (MLIC5AC), gelsolin (GSN), polymeric immunoglobulin receptor (PIGR), transcobalamin-1 (TCN 1), lysyl oxidase homolog 4 (LOXL4), kallikrein-10 (KLK10), cadherin-6 (CDH6), secreted and transmembrane protein 1 (SECTM1), BPI fold-containing family B member 1 (BRIFB1), complement factor B (CFB), metalloproteinase inhibitor 1 (TIMP1), antileukoproteinase (SLP1), dipeptidyl peptidase 1 (CTSC), serpin B6 (SERPINB6), pigment epithelium-derived factor (SERPINF1), serpin B4 (SERPINB4), neutrophil gelatinase-associated lipocalin (LCN2), serpin B3 (SERPINB3) and combinations thereof In any of the methods or uses described herein, the presence of one or more IL-13 induced proteins is selected from the group consisting of FCGBP, ALOX15, PAI2, POSTN, CST1, LYZ, ITLN1, CA2, 1TLN2, CSTA, MSLN, MUC5A, TCN1, LOXL4, KLK10 and combinations thereof in the sample from the subject as compared to the control sample identifies the subject has having or at risk of having a Th2 airway inflammatory disease.

In any of the methods or uses described herein, a higher level of one or more IL-13 induced proteins is selected from the group consisting of GSN, PIGR, CDH6, SCETM1, BPIFB1, CFB, TIMP1, SLP1, CTSC, SREPINB6, SERPINF1, SERPINB4, LCN2, SERPINB3 and combinations thereof as compared to the control sample identifies the subject has having or at risk of having a Th2 airway inflammatory disease In any of the methods or uses described herein, the subject identified as having a type-2 (Th2) airway inflammatory disease is administered an inhaled corticosteroid In any of the methods or uses described herein, the subject identified as having a Th2 airway inflammatory disease is administered a Th2 pathway inhibitor drug.

In any of the methods or uses described herein, the Th2 pathway inhibitor is selected from the group consisting of an anti-OX40L antibody, an anti-TSLP antibody, an anti-TSLRP antibody and fingolimid (FTY720).

BRIEF DESCRIPTION OF THE DRAWINGS

FIG. 7A shows results for immunoglobulin G (IgG) Fc-receptor binding protein (FCGBP) (Log FC=7.02; p-value=9.58E-11). FIG. 7B shows results for Gelsolin (GNS also referred to as GELS) (Log FC=1.05; p-value=2.02E-15). FIG. 7C shows results for arachidonate 15-lipoxygenase (ALOX15) (Log FC=6.6; p-value=8.10E-10). FIG. 7D shows results for polymeric immunoglobulin receptor (PIGR) (Log FC=1.06; p-value=1.55E-13). FIG. 7E shows results for plasminogen activator inhibitor 2 (PAI2 also referred to as SERPINB2) (Log FC=6.16; p-value=3.46E-16). Proteins that were found to be specific and unique to IL-13 stimulation: FCGBP, ALOX15, and PAI2. Proteins that were highly upregulated in response to IL-13 stimulation: GSN and PIGR. Each dot represents a unique donor.

DETAILED DESCRIPTION OF THE INVENTION

Figure 1:
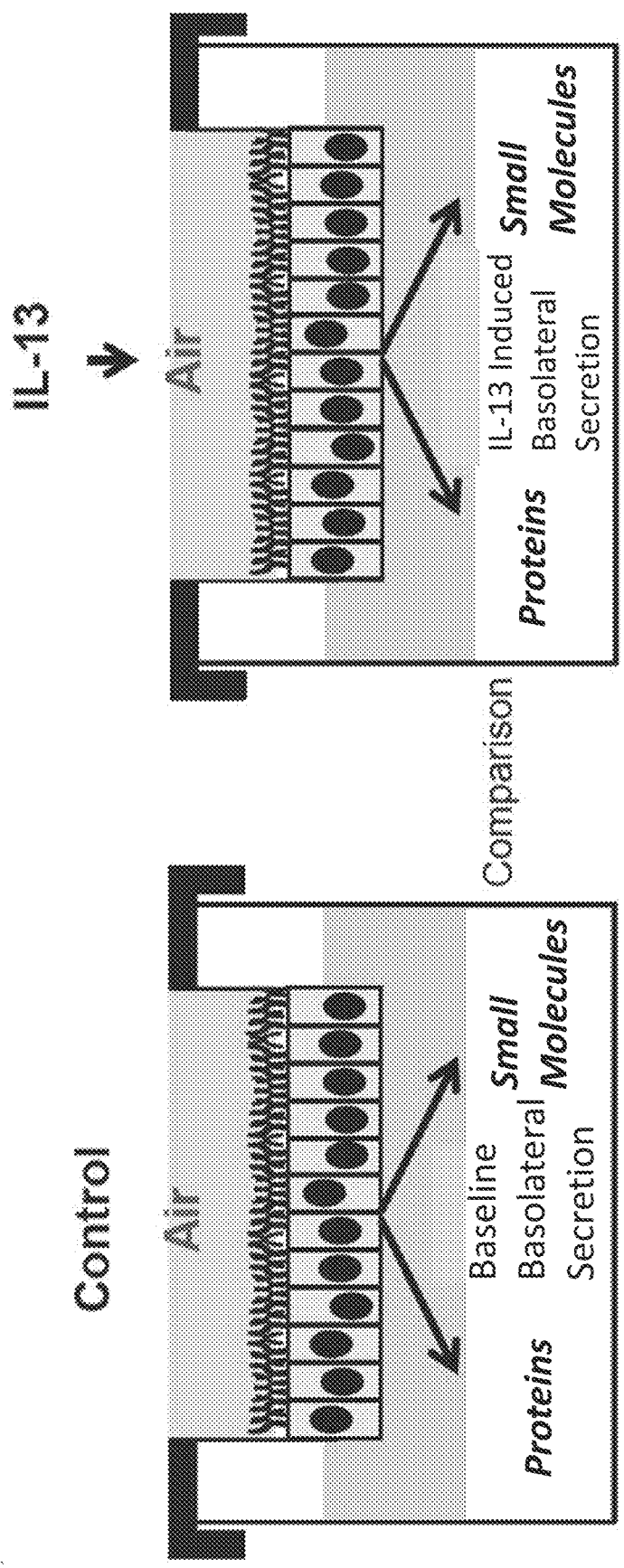
FIG. 1 shows an air-liquid interface (AU) airway epithelial culture model. Paired cultures from each donor are mock (control) and IL-13 treated, after which basolateral media is evaluated for secreted proteins and small molecules.

The present invention generally relates to novel methods for identifying, diagnosing and/or treating subjects having an inflammatory disease of the airway. These diseases can include allergic diseases as well as asthma and specifically, airway inflammatory diseases classified as Th2-high (IL-13 driven) airway inflammatory diseases, including Th2-high asthma.

The inventors have made the novel finding that the presence and/or a higher (elevated or upregulated) level of one or more IL-13 induced proteins in a blood sample from a subject, can serve as biornarker(s) for subjects having or who are at risk of having a Th2 airway inflammatory disease. In addition, the inventors have determined that the RNA expression level of these IL-13 induced proteins is correlated.

As disclosed in the Example section, the inventors have successfully optimized culture methods in order to obtain more consistent and biologically relevant ALI cultures, developed IL-13 stimulation models, optimized and normalized the collection and preparation of samples for both proteomic and metabolomics analysis, identified products that are both upregulated upon and significant to IL-13 stimulation over the course of 5-day and 10-day stimulations, and developed predictive targeted plasma assays for the IL-13-induced proteins disclosed herein.

Further, the inventors have identified protein biomarkers that are specific to Th2-high asthma and absent from healthy patients. These proteins are both stimulated in and unique to the IL-13 secretome. Included in these unique IL-13 induced proteins are Intelectin-1 and 2 in which specific single nucleotide polymorphisms (SNPs) in the gene have been linked the asthma risk (Pemberton, A. D., et al., single-nucleotide polymorphism in intelectin 1 is associated with increased asthma risk. J Allergy Clin Immunol, 2008. 122 (5): p. 1033-4) and IgG-Fc receptor binding protein (FCGBP), which has a potential role in mucosal structure maintenance. Additionally, proteins including ALOX15 and the variety of cystatins disclosed herein are described to be mediators of inflammation in a variety of diseases including asthma and chronic obstructive pulmonary disease (COPD) (Cimerman, N., et al., Serum cystatin C, a potent inhibitor of cysteine proteinases, is elevated in asthmatic patients. Clin Chim. Acta, 2000. 300(1-2): p. 83-95, Choy, D. F., et al., Gene expression patterns of Th2 inflammation and intercellular communication in asthmatic airways. J Immunol, 2011. 186(3): p. 1861-9).

The IL-13-induced proteins identified herein (see Table 1) are accessible to the blood stream. Utilizing in vitro cultured bronchial epithelial cells and by analyzing the basolateral secretome in response to IL-13 stimulation over the course of 10 days the inventors have found that IL-13 stimulation significantly alters the basolateral secretome of in vitro cultured differentiated cell cultures and that there is a global and distinct change seen between control and IL-13 stimulated cultures. IL-13 upregulates a variety of proteins in vitro. The inventors have found 29 proteins that are significantly upregulated in response to IL-13 stimulation in vitro and that 18 proteins are unique and specific to only IL-13 stimulated cultures (indicating that these proteins are absent in the controls but were detected in the IL-13 stimulation) or were nearly specific (indicating that they are absent in all but a few controls, and detected in IL-13 stimulations). Others proteins were present in the controls, but were significantly upregulated in IL-13 stimulations (labeled as "upregulated"). These proteins can be used as serum biomarkers to predict and stratify patients who have Th2 airway inflammatory diseases, such as Th2-high asthma from those who do not.

TABLE 1

| Protein Accession | Protein Name | Gene Symbol | log2 Fold Change | p-value adjusted | Protein Specificity to IL-13 Stimulation | | |
|---|---|---|---|---|---|---|---|
| | | | | | Specific/ Unique | Nearly Specific | Up-regulated |
| FCGBP | IgGFc-binding protein | FCGBP | 6.4669 | 1.34E−18 | X | | |
| PAI2 | Plasminogen activator inhibitor 2 | SERPINB2 | 6.1687 | 3.46E−16 | X | | |
| LOX15 | Arachidonate 15-lipoxygenase | ALOX15 | 6.1458 | 3.46E−16 | X | | |
| POSTN | Periostin | POSTN | 5.5146 | 1.46E−12 | X | | |
| CYTN | Cystatin-SN | CST1 | 5.4339 | 7.01E−12 | X | | |
| LYSC | Lysozyme C | LYZ | 5.1713 | 2.48E−10 | X | | |
| ITLN1 | Intelectin-1 | ITLN1 | 4.9355 | 1.24E−09 | X | | |
| CAH2 | Carbonic anhydrase 2 | CA2 | 4.3741 | 3.12E−10 | | X | |
| ITLN2 | Intelectin-2 | ITLN2 | 4.0120 | 1.38E−05 | X | | |
| CYTA | Cystatin-A | CSTA | 3.9282 | 2.15E−05 | X | | |
| MSLN | Mesothelin | MSLN | 2.9180 | 0.0044 | X | | |
| MUC5A | Mucin-5AC | MUC5AC | 2.7198 | 0.0002 | | X | |
| TCO1 | Transcobalamin-1 | TCN1 | 2.6586 | 0.0064 | | X | |
| LOXL4 | Lysyl oxidase homolog 4 | LOXL4 | 2.5558 | 0.0086 | | X | |
| KLK10 | Kallikrein-10 | KLK10 | 2.1966 | 0.0048 | | X | |
| CADH6 | Cadherin-6 | CDH6 | 2.1714 | 0.0002 | | | X |
| SCTM1 | Secreted and transmembrane protein 1 | SECTM1 | 1.7358 | 0.0321 | | | X |
| BPIB1 | BPI fold-containing family B member 1 | BPIFB1 | 1.5612 | 8.78E−05 | | | X |
| CFAB | Complement factor B | CFB | 1.1161 | 4.18E−05 | | | X |
| TIMP1 | Metalloproteinase inhibitor 1 | TIMP1 | 1.0901 | 0.0018 | | | X |
| SLPI | Antileukoproteinase | SLPI | 0.9653 | 0.0361 | | | X |
| PIGR | Polymeric immunoglobulin receptor | PIGR | 0.9618 | 6.45E−16 | | | X |
| GELS | Gelsolin | GSN | 0.9506 | 3.24E−16 | | | X |
| CATC | Dipeptidyl peptidase 1 | CTSC | 0.8895 | 0.0021 | | | X |

TABLE 1-continued

| Protein Accession | Protein Name | Gene Symbol | log2 Fold Change | p-value adjusted | Protein Specificity to IL-13 Stimulation | | |
|---|---|---|---|---|---|---|---|
| | | | | | Specific/ Unique | Nearly Specific | Up-regulated |
| SPB6 | Serpin B6 | SERPINB6 | 0.8751 | 0.0026 | | | X |
| PEDF | Pigment epithelium-derived factor | SERPINF1 | 0.6200 | 0.0054 | | | X |
| SPB4 | Serpin B4 | SERPINB4 | 0.4915 | 2.15E−05 | | | X |
| NGAL | Neutrophil gelatinase-associated lipocalin | LCN2 | 0.3980 | 0.0286 | | | X |
| SPB3 | Serpin B3 | SERPINB3 | 0.2988 | 0.0028 | | | X |

The term "sample" or "patient sample" or "subject sample" or "test sample" can be used generally to refer to a sample of any type which contains products that are to be evaluated by the present methods, including but not limited to, a blood sample, a sample of isolated cells, a tissue sample and/or a bodily fluid sample. A biological sample can include any bodily fluid or tissue from a subject that may contain the proteins contemplated herein, as well as the RNA and genes that encode the proteins. In some embodiments, the sample may comprise blood, plasma or peripheral blood mononuclear cells (PBMCs), leukocytes, monocytes, lymphocytes, basophils or eosinophils. In a preferred aspect, the biological sample is blood. In one aspect, the methods of the present invention can be performed on an ex vivo biological sample.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated (or increased) as compared to a control, downregulated as compared to a control, or unchanged as compared to a control or increased or decreased as compared to a reference or control level. Therefore, the step of detecting or determining expression does not require that expression of the gene actually is upregulated or downregulated or increased or decreased, but rather, can also include detecting or determining that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (FCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: mass spectrometry, Western blot, immunoblot, enzyme-linked immunosorhant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners, Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, Anal. Biochem. 212:457; Schuster et al., 1993 Nature 365: 343). Other suitable assays for measuring the binding of one protein to another include, for example, immunoassays such as enzyme linked immunoabsorbent assays (HASA) and radioimmunoassays (RIA); or determination of binding by monitoring the change in the spectroscopic or optical properties of the proteins through fluorescence, UV absorption, circular dichroism, or nuclear magnetic resonance (NMR).

In one aspect, an upregulated, higher or elevated level of the one or more IL-13 induced proteins disclosed herein, is determined when the subject's level is at least greater than one standard deviation from the mean as compared to the control level of the same one or more IL-13 induced proteins and/or is determined to be significantly different (i.e., statically significantly different) and/or is higher than normal or established levels of the one or more IL-13 induced proteins from the control levels.

In still other aspects, the level of the one or more IL-13 induced proteins disclosed herein is at least about 5%, at least about 10%, at least about 20%, at least about 30%, at least about 40%, at least about 50%, at least about 60%, at least about 70%, at least about 80%, at least about 90%, or 100% higher, elevated or upregulated from the control level of the same protein. In still another aspect, the level of the one or more IL-13 induced proteins disclosed herein is at least about 2-fold, at least about 3-fold, at least about 4 fold, at least about 5 fold, at least about 10-fold, at least about 20 fold, at least about 25 fold, at least about 30 fold, at least about 40 fold, at least about 50 fold or 100 fold higher (or upregulated by the fold amount) from the control level.

In one aspect, the level and/or presence of one or more IL-13 induced proteins can be determined as compared to the level of the same protein from a control. In still another aspect, the level of two IL-13 induced proteins can be determined and compared to the level of the same two proteins from a control. In yet another aspect, the level of 3, 4, 5, 6, 7, 8, 9, 10, 11, 12, 13. 14, 15, 16, 17. 18, 19, 20, 21, 22, 23, 24, 25, 26, 27, 28, and 29 IL-13 induced proteins disclosed herein can be determined and compared to the corresponding proteins from a control.

In one aspect, the IL-13 induced proteins is selected from the group consisting of IgG Fc-receptor binding protein (FCGBP), arachidonate 15-lipoxygenase (ALOX15), plasminogen activator inhibitor 2 (PAI2), carbonic anhydrase 2 (CA2), cystatin CN (CST1), periostin (POSTN), lysozyme C (LYZ), intelectin-1 (ITLN1), calcium-activated chloride channel 1 (CLCA1), intelectin-2 (ITLN2), cystatin A (CSTA), mesothelin (MSLN), ST6 beta-galactosamide alpha-2,6-sialyltransferase 1 (SIAT1), mucin 5AC (MUC5AC), gelsolin (GSN), polymeric immunoglobulin receptor (PIER), transcobalamin-1 (TCN1), lysyl oxidase homolog 4 (LOXL4), kallikrein-10 (KLKI 10), cadherin-6 (CDH6), secreted and transmembrane protein 1 (SECT1V11), BPI fold-containing family B member 1 (BPIFB1), complement factor B (CFB), metalloproteinase inhibitor 1 (TIMP1), antileukoproteinase (SLP1), dipeptidyl peptidase 1 (CTSC), serpin B6 (SERPINB6), pigment epithelium-derived factor (SERPINF1), serpin B4 (SERPINB4), neutrophil gelatinase-associated lipocalin (LCN2), serpin B3 (SERPINB3) and combinations thereof In yet another aspect, the presence of one or more IL-13 induced proteins is selected from the group consisting of FCGBP, ALOX15, PAI2, POSTN, CST1, LYZ, ITLN1, CA2, ITLN2, CSTA, MSLN, MUC5A, TCN1, LOXL4, KLK10 and combinations thereof as compared to corresponding control levels of the same protein or proteins. In addition, the gene expression of one or more IL-13 induced proteins is selected from the group consisting of FCGBP, ALOX15, PAI2, POSTN CST1, LYZ, ITLN1, CA2, ITLN2, CSTA, MSLN, MUC5A, TCN1, LOXL4, KLK10 and combinations thereof and can be compared to the expression level of the corresponding gene or genes from a control.

In one aspect, a higher (or elevated) level of one or more IL-13 induced proteins is detected wherein the one or more IL-13 induced proteins is selected from the group consisting of GSN, PIGR, CDH6, SCETM1, BPIFB1, CFB, TIMP1, SLP1, CTSC, SREPINB6, SERPINF 1, SERPINB4, SERPINB3 and combinations thereof and compared to a control sample of the same one or more proteins. In addition, an elevated gene expression level of the one or more IL-13 induced proteins is detected wherein the one or more IL-13 induced proteins is selected from the group consisting of FCGBP, ALOX15, PAI2, POSTN, CST1, LYZ, ITLN1, CA2, ITLN2, CSTA, MSLN, MUC5A, TCN1, LOXL4, KLK10 and combinations thereof as compared to corresponding expression levels from a control.

Over the comprehensive se of completed data obtained by the inventors from optimized cultures and exposures, between 900-2000 peptides/sample were detected, equating to 200-350 proteins/sample and representing a total of 662 distinct proteins across the data set. Multi-dimensional scaling (MDS) analysis demonstrates that at the global level there is a vastly different response elicited from ALI cultures being stimulated with IL-13 versus mock-stimulation. Differential expression analysis was conducted on peptide counts resulting from each stimulated donor pair and heat map clustering indicated a distinct grouping of BSA samples, separate from samples stimulated with IL-13 over both 5- and 10-day stimulations. From differential expression analysis, the inventors identified a total of 29 proteins that are significantly up-regulated within the secretome of bronchial epithelial cells stimulated with IL-13 during both exposure models. Furthermore, of those, 18 are both significantly upregulated and unique to IL-13 stimulated samples, with no peptides from the proteins of interest being detected in the mock-treated secretome samples (Table 1). In addition, RNA-seq expression profiling has been done demonstrating the relationship between the levels of proteins detected in the conditioned media secretome and the RNA expression level. These data demonstrate that there is a positive correlation between the protein level detected within the secretome samples and the RNA expression level within the same donor AIL cultures, thus demonstrating that IL-13-stimulated products are not only increased at the protein level, but at the RNA level as well.

In still another aspect, one or more IL-13 induced proteins are detected in the blood sample from the subject and are absent (i.e., not present) in the control sample, When comparing the protein level and/or the RNA expression level to the control protein level or control RNA expression level, it is to be understood that the level of the one or more IL-13 induced proteins (or the corresponding RNA expression level) is compared with the same protein from the control. For example, if the expression level of FCGBP and ALOX15 are both determined or analyzed, then the level of FCGBP from the subject would be compared to the level of FCGBP from the control and likewise, the level of ALOX15 from the subject would be compared to the level of ALOX15 from the control.

In some aspects of the invention, the subjects can be treated by administration of one or more compounds including but not limited, corticosteroids, Th2 pathway inhibitors, leukotriene antagonists, anti-cytokine antibodies, anti-cytokine receptor antibodies, anti-IgE antibody, JAK kinase inhibitors, antibiotics, a phosphodiesterase inhibitor, and combinations thereof. In one aspect, the Th2 pathway inhibitor is selected from the group consisting of an anti-OX40L antibody (for example Ocelumab), an anti-TSLP antibody (for example AMG 157), and anti-TSLPR antibody (for example RG7258) and fingolimid (FTY720) and combinations thereof.

As used herein, reference to a reference or control, means a subject who is a relevant reference or control to the subject being evaluated by the methods of the present invention. The control can be matched in one or more characteristics to the subject. In one aspect, the control can be an individual with no history of an airway inflammatory disease such as a Th2-high airway inflammatory disease, such as Th2-high asthma. In one aspect, the control does not have Th2-high asthma. In another aspect, the control has been determined to be asthma-free. The control can be matched in one or more of the following characteristics, gender and age. The reference or control protein and/or RNA expression level used in the comparison of the methods of the present invention can be determined from one or more relevant reference or control subjects.

In other various aspects of the invention, the subject can be treated for an inflammatory disease of the airways, such as for a Th2-high inflammatory disease of the airway, including but not limited to Th2-high asthma, by various methods including but not limited to, administration of a Th2 pathway inhibitor drug, a bronchodilator, an inhaled corticosteroid, administration of a phosphodiesterase inhibitor, administration of an antibiotic, administration of prednisone, antibiotics, pulmonary rehabilitation, oxygen therapy, and combinations thereof, as well as, by known standard of care methods for the diseases. In one aspect, known standard treatment methods including those described above, are used in the treatment of subjects identified by the methods of the present invention.

Another embodiment of the present invention relates to a method to predict or determine the response of a subject to treatment with a Th2 pathway inhibitor and/or a corticosteroid. In one aspect, the subject has or is at risk of developing a Th2 airway inflammatory disease, such as Th2-high asthma. In one aspect, a biological sample, such as blood, is obtained from the subject. The level of one or more IL-13 induced proteins in the sample is determined and compared to a control sample wherein the presence and/or a higher level of the one or more IL-13 induced proteins as compared to the control sample identifies the subject as having or at risk of having a Th2 airway inflammatory disease responsive to treatment with a Th2 pathway inhibitor. In one aspect, the one or more IL-13 induced proteins is selected from the group consisting of FCGBP, ALOX15, PAI2, CA2, CST1, POSTN, lysozyme C LYZ), ITLN1, CLCA 1, ITLN2, CSTA, MSLN, SIAT1, MUC5AC, GSN, PIGR, TCN1, LOXL4, KLK10, CDH6, SECTM1, BPIFB1, CFB, TIMP1, SLP1, CTSC, SERPINB6, SERPINF 1, SERPINB4, LCN2, SERPINB3 and combinations thereof. In one aspect, the subject identified as having a Th-2 airway inflammatory disease responsive to treatment with a Th2 pathway inhibitor and/or a corticosteroid is administered a Th2 pathway inhibitor and/or a corticosteroid. The Th2 pathway inhibitor can be is selected from the group consisting of an anti-OX40 L antibody, an anti-TSLP antibody, an anti-TSLRP antibody and fingolimid (FTY720).

Another embodiment of the present invention relates to a method of endotyping a subject as having Th2-high asthma. In one aspect, a biological sample, such as a blood sample is obtained from the subject. The level of one or more IL-13 induced proteins (and/or the corresponding RNA expression level) disclosed herein is determined in the sample and compared to a control level of the same IL-13 induced protein(s), wherein the presence and/or a higher level of the one or more IL-13 induced proteins from the subject as compared to the control sample identifies the subject has having Th2-high asthma In one aspect, the one or more IL-13 induced proteins is selected from the group consisting of PCGBP, ALOX15, PAI2, CA2, CST1, POSTN, lysozyme. C LYZ), LTLN1, CLCA 1, ITLN2, CSTA, MSLN, SIAT1, MUC5AC, GSN, PIGR, TCN1, LOXL4, IKILK10, CDH6, SECTM1, BPIFB1, CFB, TRIP1, SLP1, CTSC, SERPINB6, SERPINF1, SERPINB4, LCN2, SERPINB3 and combinations thereof. In one aspect, the subject identified as having Th2-high asthma is administered a corticosteroid. In one aspect, the subject is administered a Th2 pathway inhibitor. The Th2 pathway inhibitor can be is selected from the group consisting of an anti-OX40 L antibody, an anti-TSLP antibody, an anti-TSLRP antibody and fingolimid (FTY720).

Another embodiment of the present invention relates to a kit for detecting the presence, level and/or expression of one or more of the IL-13 induced proteins and/or RNA levels disclosed herein. In one aspect, the kit comprises a detection agent for detecting the expression of one or more genes. In one aspect, the kit comprises an agent for detecting the RNA expression. In still another aspect, the kit comprises an agent for detecting protein expression of the one or more IL-13 induced proteins disclosed herein.

In some aspect, the kits can comprise an antibody, detection ability, and quantification ability. In still other aspects, the detection ability includes immunoflourescence. In one aspect, the kit comprises at least one antibody that specifically recognizes a protein selected from the group consisting of FCGBP, ALOX15, PAI2, CA2, CST1, POSTN, lysozyme C LYZ), ITLN1, CLCA 1, ITLN2, CSTA, MSLN, SIAT1, MUC5AC, GSN, PIGR, TCN1, LOXL4, KLK10, CDH6, SECTM1, BPIFB1, CFB, TIMP1, SLP1, CTSC, SERPINB6, SERPINF1, SERPINB4, LCN2, SERPINB3 and combinations thereof. In another aspect, a kit comprises at least one anti-sense RNA corresponding to a protein selected from the group consisting of FCGBP, ALOX15, PAI2, CA2. CST1, POSTN, lysozyme C LYZ), ITLN1, CLCA 1, ITLN2, CSTA, MSLN, SIAT1, MUC5AC, GSN, PIGR, TCNI, LOXL4, KLK10, CDH6, SECTM1, BPIFB1, TIMP1, SLP 1, CTSC, SERPINB6, SERPINF1, SERPINB4, LCN2, SERPINB3 and combinations thereof. In still another aspect, a kit comprises a microfluidics system comprising one or more tags fix identifying against a protein selected from the group consisting of FCGBP, ALOX15, PAI2, CA2, CST1, POSTN, lysozyme C LYZ), ITLN1, CLCA 1, ITLN2, CSTA, MSLN, SIAT1, MUC5AC, GSN, PIGR, TCN1, LOXL4, KLK10, SECTM1, BPIFB1, CFB, TIMP1, SLP1, CTSC, SERPINB6, SERPINF1, SERPINB4, LCN2, SERPINB3 and combinations thereof. In yet another aspect, a kit for determining the expression level of at least one protein is selected from the group consisting of FCGBP, ALOX15, PAI2, CA2, CST1, POSTN, lysozyme C LYZ), ITLN1, CLCA 1. ITLN2, CSTA, MSLN, SIAT1, MUC5AC, GSN, PIGR, TCN1, LOXL4, KLK10, CDH6, SECTM1, BPIFB1, CFB, TIMP1, SLP1, CTSC, SERPINB6, SERPINF1, SERPINB4, LCN2, SERPINB3 and combinations thereof, wherein the kit comprises a component selected from an antibody, an antisense. RNA molecule and a microfluidics system, wherein in the component detects the expression level of the least one IL-13 induced protein or RNA level. In still another aspect, a kit is for predicting a subject's risk of having a Th2 airway inflammatory disease comprising at least one antibody that specifically recognizes a protein selected from FCGBP, ALOX15, PAI2, CA2, CST1, POSTN, lysozyme C LYZ), ITLN1, CLCA 1, ITLN2, CSTA, MSLN, SIAT1, MUC5AC, GSN, PIOR, TCN1, LOXL4, KL1(10, CDH6, SECTM1, BPIFB1, CFB, TIMP1, SLP1, CTSC, SERPINB6, SERPINF1, SERPINB4, LCN2, SERPINB3 and combinations thereof wherein recognition or elevation of the protein predicts the subject is at risk of the disease. In another aspect, a kit is for predicting a subject's risk of having a Th2 airway inflammatory disease comprising at least one anti-sense RNA corresponding to a protein selected from the group consisting of FCGBP, ALOX15, PAI2, CA2, CST1, POSTN, lysozyme C LYZ), ITLN1, CLCA 1, ITLN2, CSTA, MSLN, SIAT1, MUC5AC, GSN, PIGR, TCN1, LOXL4, KLK10, CDH6, SECTM1, BPIFB1, CFB, TEMP1, SLP1, CTSC, SERPINB6, SERPINF1, SERPINB4, I.CN2, SERPINB3 and combinations thereof, wherein the presence or elevated level of the protein predicts the subject is at risk of having the disease. In yet another aspect, a kit is for predicting a subject's risk of a Th2 airway inflammatory disease comprising a microfluidics system comprising one or more tags for identifying against a protein selected from the group consisting of FCGBP, ALOX15, PAI2, CA2, CST1, POSTN, lysozyme C LYZ), ITLN1, CLCA 1, ITLN2, CSTA, MSLN, SIAT1, MUC5AC, GSN, PIGR, TCN1, LOXL4, KLK10, CDH6, SECTM1, BPIFB1, CFB, TIMP1, SLPT, CTSC, SERPINB6, SERPINF1, SERPINB4, LCN2, SERPINB3 and combinations thereof, wherein identification or elevated level of the protein predicts the patient is at risk of the disease.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no 30 inconsistency with the present disclosure.

EXAMPLES

Example 1 shows the basolateral small molecule and protein secretome of differentiated airway epithelial cells from healthy and asthmatic subjects at baseline and in response to IL-13.

Bronchial epithelial cell lines from 10 adult asthmatics and 10 controls currently housed within an established biohank are expanded and differentiated at air-liquid interface (ALI). These well-differentiated ALI cultures are IL-13 treated and mock-treated (FIG. 1). The basolateral (mimicking human airway basement membrane side) media is collected and screened for small molecules and proteins by mass spectrometry profiling. The cultures are compared to identify small molecules and proteins secreted selectively or at differential levels in the IL-13-versus mock-treated cultures and differences between epithelial cultures from asthmatic versus healthy subjects is also determined.

A. Procurement of Airway Epithelial Samples

Bronchial airway epithelial cells were collected from bronchial brushings and cultured then cryopreserved by the Human Cell Core/Mucosal Immunity Program at National Jewish Health (NJH). In total, 25 donor samples of bronchial airway epithelial cells were obtained from 10 healthy controls and 15 asthmatic donors all classified as non-smokers. Through optimization of the air-liquid interface (ALI) culture model, differentiated epithelial AL1 cultures from 6 healthy donor samples and 13 asthmatic donor samples (Table 2.) were obtained, which were used for IL-13 stimulation and data collection and analysis.

TABLE 2

Human Bronchial Cell Donors

| Donor | Sex | Age | Disease State |
|---|---|---|---|
| HBEC 153173 | Male | 48 | Healthy |
| HBEC 153741 | Female | 62 | Healthy |
| HBEC 155404 | Female | 71 | Healthy |
| HBEC 153109 | Male | 27 | Healthy |
| HBEC 156680 | Male | 42 | Healthy |
| HBEC 153870 | Female | 35 | Healthy |
| HBEC 153724 | Male | 49 | Asthmatic |
| HBEC 154741 | Male | 62 | Asthmatic |
| HBEC 154711 | Female | 72 | Asthmatic |
| HBEC 154142 | Female | 23 | Asthmatic |
| HBEC 154651 | Female | 35 | Asthmatic |
| HBEC 153087 | Female | 39 | Asthmatic |
| HBEC 153832 | Female | 24 | Asthmatic |
| HBEC 154417 | Male | 73 | Asthmatic |
| HBEC 156466 | Female | 42 | Asthmatic |
| HBEC 154717 | Female | 44 | Asthmatic |
| HBEC 154783 | Female | 55 | Asthmatic |
| HBEC 152328 | Male | 72 | Asthmatic |
| HBEC 154566 | Female | 37 | Asthmatic |

B. Optimization of Airway Epithelial Cell (AEC) Culture and Differentiation

The ability of the epithelial cell monolayers to polarize and differentiate depends on a variety of factors including the collagen matrix the cells are seeded on, the density at which the cells are initially plated, and the proliferation and differentiation medias used over the duration of the culture. The inventors first optimized their collagen coating procedures in order to ensure maximal collagen coverage across the well at the time of cell seeding. The protocol being used ensures that the collagen has sufficient time to form a matrix on the apical surface of the membrane. Excess wash steps were eliminated, in the event that the excessive washing was adversely affecting the collagen layer. Lastly, it was determined that drying of the collagen prior to cell seeding can lead to cracks in the collagen coating, with subsequent release of cells within the monolayer.

To seed transwell inserts, cells can be plated at low levels and allowed to grow into a monolayer on the membrane, or they can be seeded at 100% density and allowed to settle onto the membrane in a tight monolayer. Bronchial epithelial cells were seeded across a range of densities from $2.0 \times 10^4$ to $8.0 \times 10^4$ cells/insert, allowing the cells to expand and grow into a monolayer, or from $1 \times 10^5$ to $1.2 \times 10^5$ cells/insert and observing the integrity of the intact monolayer after 24 hours. From these trials, it was found seeding at a density of $2 \times 10^4$ cells/insert resulted in optimal monolayer formation. This seeding density allows the seeded cells to proliferate within the insert to form a tight, intact monolayer which produces the highest level of transepithelial electrical resistance prior to establishing the air-liquid interface.

The media and its components have a significant effect on how well the cells proliferate and differentiate while in ALI culture. In order to obtain the most differentiated monolayers for the optimal airway epithelial cell model, 3 different media preparations were compared in their ability to derive well-differentiated cultures. Various donors were cultured in AM1 (expansion)/AM2 (differentiation) media (Wu, R, Y. H. Zhao, and M. M. Chang, Growth and differentiation of conducting airway epithelial cells in culture. Eur Respir J. 1997. 10(10): p. 2398-403) Chu media (Chu, H. W., et at, CRISPR-Cas9-mediated gene knockout in primary human airway epithelial cells reveals a proinflammatory role for MUC18. Gene Ther, 2015. 22(10): p. 822-9), or PneumaCult-ALI (PC-ALI) complete media (Karp, P. H., et al., An in vitro model of differentiated human airway epithelia. Methods for establishing primary cultures. Methods Mol Biol, 2002. 188: p. 115-37), as per their respective published protocols.

Figure 2:
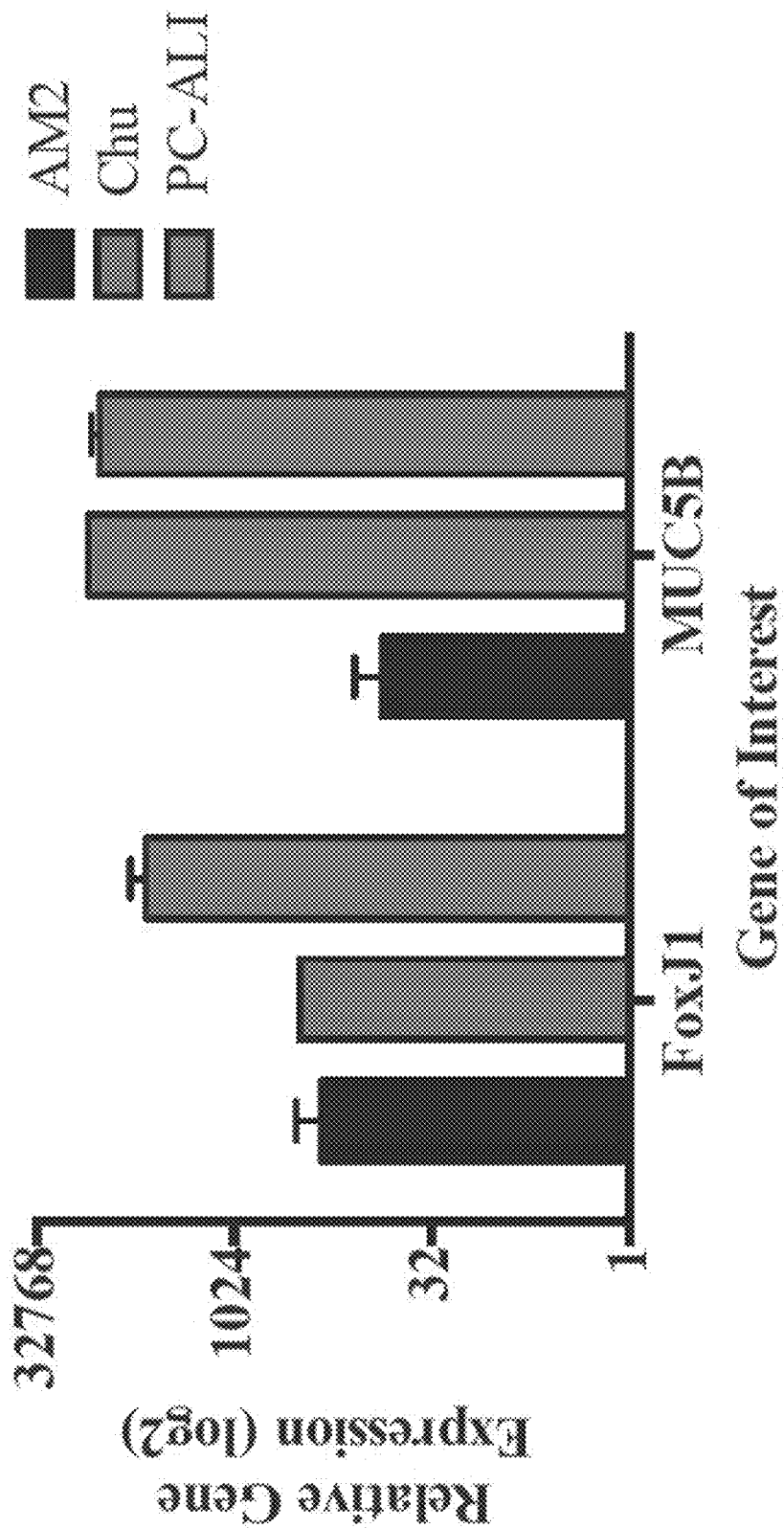
FIG. 2 shows expression of differentiation genes forkhead box J1 (FOXJ1) and mucin 5B (MUC5B) in ALI cultures grown in different media conditions. AM2 media is shown as the first bar in each gene of interest grouping; Chu media (referred to as Chu) is shown as the second bar in each gene of interest grouping; PneumaCult ALI (PC-ALI) media is shown as the third bar in each gene of interest grouping.
Figure 3:
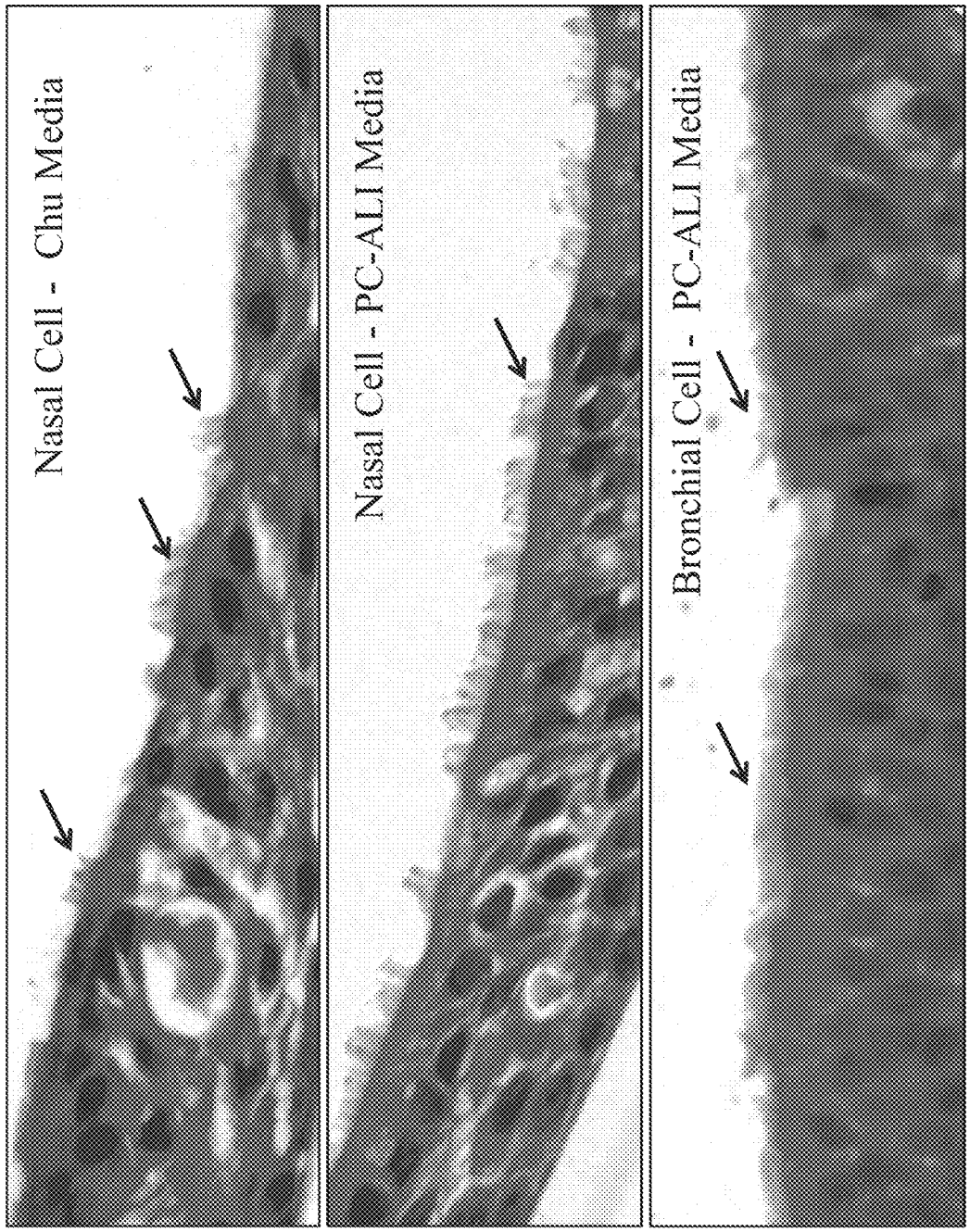
FIG. 3 shows histological comparison of ALI cultures grown for 21 days in Chu media vs. PneurnaCult ALI (PC-ALI) media.

Over the course of the 21-day air-liquid interface culture, visual observations were made on the cultures and the state of differentiation was measured using qPCR and histology. Gene expression analysis by qPCR at day 21 of ALI culture shows that PC-ALI cultured cells have a higher level of differentiation as demonstrated by higher levels of FOXJ1, the driver of ciliogenesis, as well as increased levels of the mucin gene MUC5B compared to AM1/AM2-grown cultures (FIG. 2). Hematoxylin and eosin (H&E) stained histology slides verified that the same nasal cultures grown in PC-ALI result in higher levels of cilia compared to those grown in Chu media (FIG. 3). Additionally, human bronchial epithelial cultures (HBEC) being used in this study appear to develop a super-ciliated phenotype with densely packed cilia covering almost the entirety of the apical surface of the culture (FIG. 3). Further visual observations were made that the cultures grown in PC-ALI developed a more consistent overall culture in the case of the level of cilia and mucus across the transwell membrane compared to AM1/AM2 cultured cells which resulted in patchy and inconsistent development of mucus and cilia.

In summary, from the data and observations gathered from donors cultured in both types of media, it was concluded that the optimal media to grow ALI cultures in is the PC-ALI media. The optimization of this differentiation method ensures that the epithelial cultures closely model the in vivo airway epithelium.

C. Reduction of Contaminants from Secretome Analysis Samples

The number and quantity of contaminating small molecules and proteins derived from the culture media can dramatically inhibit the detection and quantification of IL-13 secretome proteins and small molecules in the conditioned culture media samples. To eliminate such contaminants, the following optimization was conducted.

Figure 4:
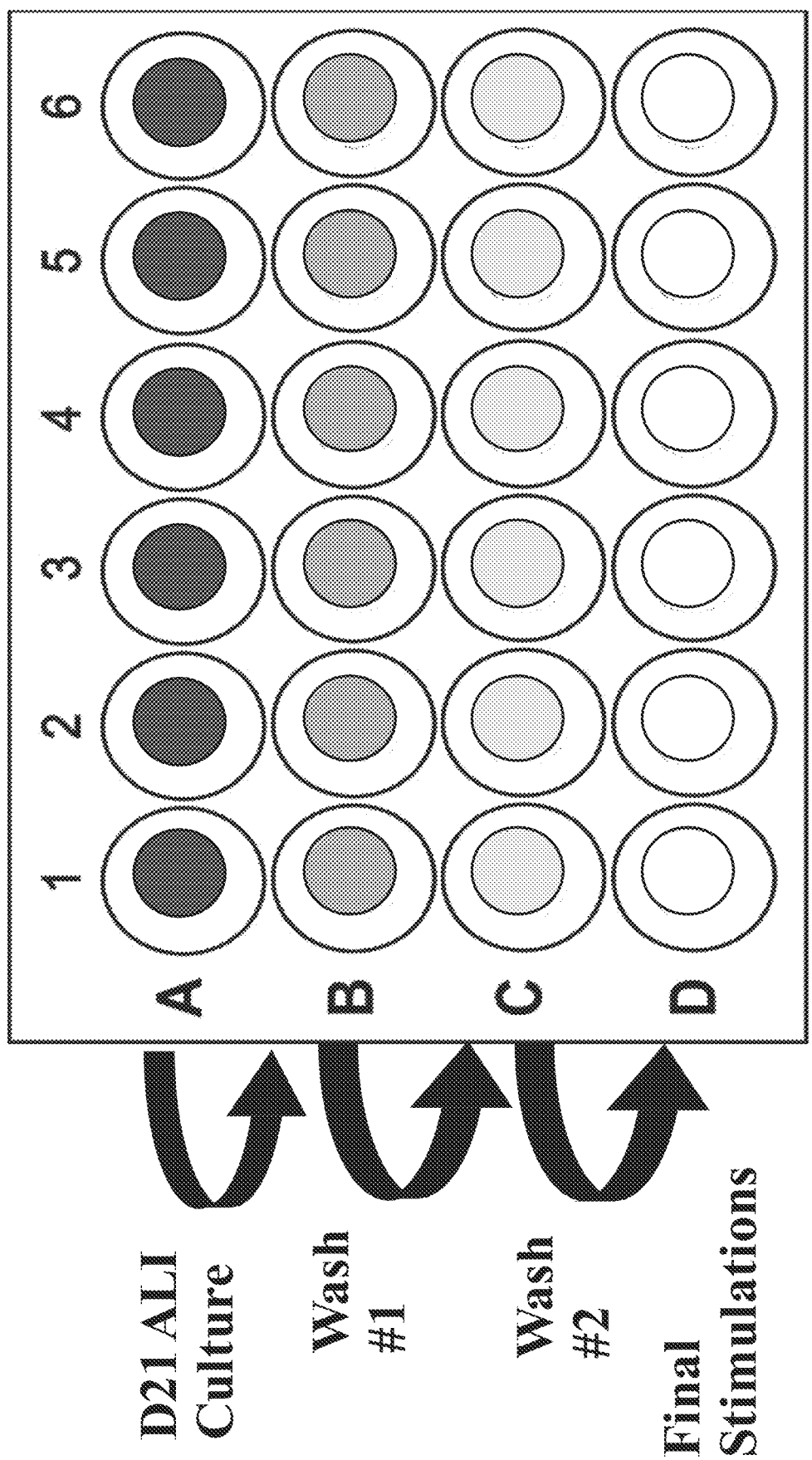
FIG. 4 shows schematic of insert wash protocol to reduce/eliminate culture media contaminants from the inserts and plastics prior to collection of conditioned media for proteomic analysis.

The inventors' original experimental design proposed to collect basolateral media from 21 day ALI cultures, which had been IL-13- or mock-stimulated in complete culture media. However, preliminary experiments indicated that the majority of the peptides identified from cultures stimulated in complete culture media were derived from bovine serum albumin (BSA), the main component of fetal bovine serum used as an additive in the complete culture media. In order to eliminate BSA, and other culture proteins and small molecules from the collected media, all supplements were removed from the basal culture media used during the final 24-hours of stimulation. Specifically, the media was depleted of all serum additives, antibiotics, and anti-fungals. Importantly, it was confirmed that the health and polarity of cultures was not compromised during this final stimulation step conducted with depleted media. Despite this, significant levels of contaminating BSA was still found in the proteomic analysis of the conditioned culture media. It is believed that BSA had coated the culture wells and transwell inserts during the prior 21 days of complete media culture. Therefore, a rigorous wash protocol was designed to reduce this potential contamination source (FIG. 4). Specifically, upon reaching day 21 of culture, each transwell insert was moved to a new, clean well of the culture plate and both the apical and basolateral chambers were washed with warmed 37° C. PBS for 10 minutes in a humidified 37° C. 5% $CO_2$ tissue culture incubator. The well transfers were included to eliminate carry-over of BSA from the well plastics, and the transfer and wash steps were then completed a second and third time. Comparing each culture method, it was determined that preliminary data resulted in bovine serum albumin peptides detected at levels of >50 peptides/sample, while peptides from serum albumin are detected at much lower levels (<10 peptides/sample) in samples collected using the described washes and protocol modifications.

Standard protocols for protein collection and storage call for the addition of protease cocktail inhibitor to the sample to prevent protein degradation. However, these inhibitors will likely be detected in the small molecule analysis and can possibly interfere with detection of epithelial cell-derived small molecules. To avoid protease inhibitor use but also preserve sample proteins it was decided to immediately process proteins and small molecules upon collection of the basolateral media. The proteins are preserved with this immediate sample processing in the absence of inhibitors, and are equally representative of proteins identified in samples in which protease inhibitor cocktail was used.

In summary, these changes to culture media, culture vessel washing, and sample processing have resulted in much cleaner secretome analysis profiles, which are described below.

D. IL-13 Stimulation Models

Modeling this in vivo airway situation in culture requires some thought with regard to the timing of the IL-13 stimulation in the in vitro culture model (FIG. 5), The stable asthmatics that have endotyped for Th2 status have a constant level of IL13 that results in sustained, smoldering inflammation of the airway epithelium. In this sense the Th2-high asthmatic airway is under a steady-state of IL-13 influence. Therefore, the first IL-13 dosing regimen ("Steady-State") was defined by two consecutive doses of IL-13 (10 ng/ml) every 24 hours with media collected at 48 hours from first dose. Supporting this "Steady-State" model reflects the effects present in a stable Th2-high asthmatic, highly overlapping gene expression profiles between stable Th2-high in vivo airway epithelium and IL-13 "Steady-State" model stimulated airway epithelial cultures was observed. In early trials, this "steady-state" exposure model was utilized, resulting in preliminary proteomics data; however, upon further model development, the extended stimulation models described below were used.

Figure 5:
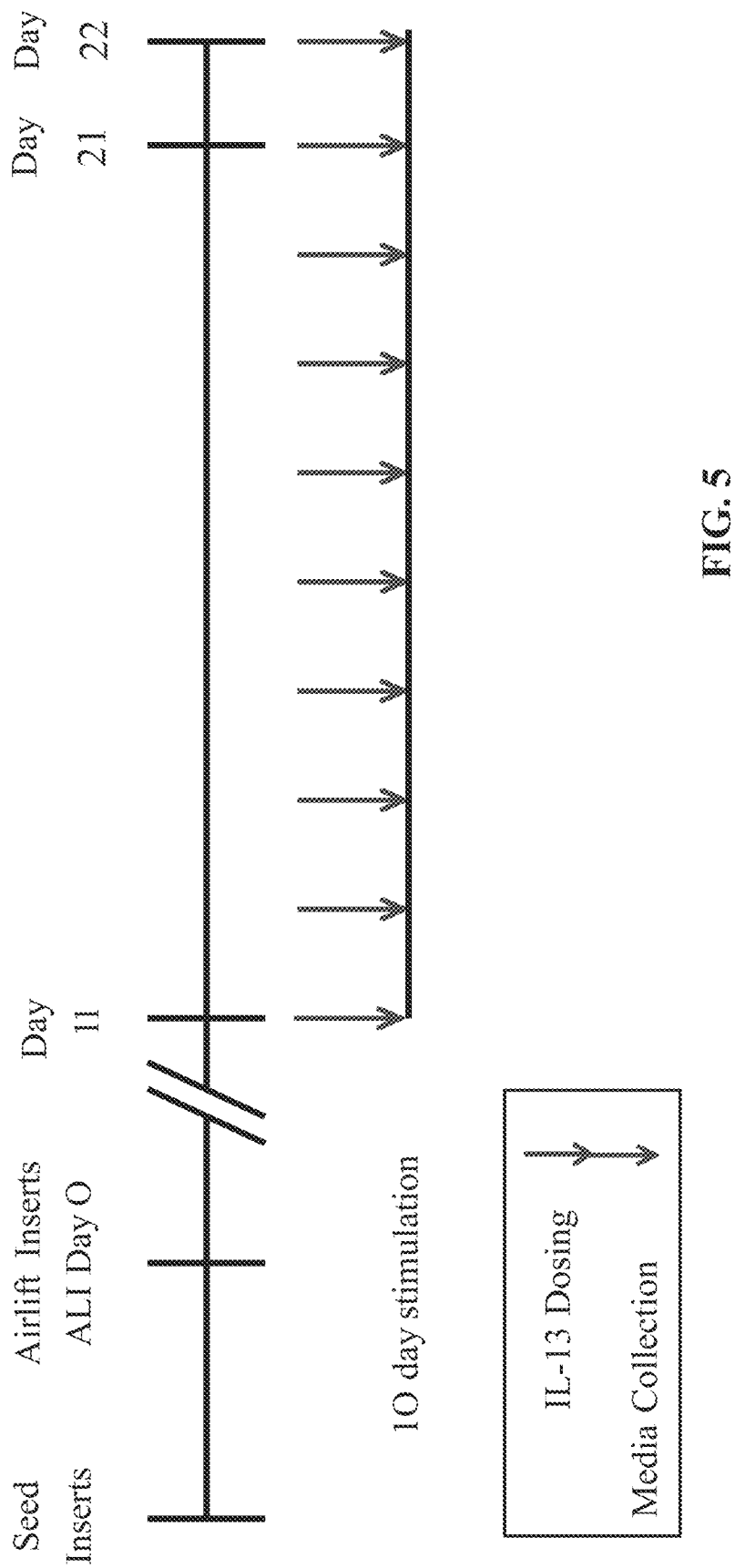
FIG. 5 shows IL-13 airway epithelial cell exposure time course models. IL-13 dosing is indicated by the arrows on Day 11 to Day 21. Media, collection is indicated by the arrow on Day 22.

Additional dosing schemes that can reflect the sustained inflammation in a stable Th2-high asthmatic at the 5-day and 10-day exposure models are illustrated in FIG. 5. These models assume that IL-13 stimulation is a sustained, ongoing process, and takes into account that the airway in vivo is constantly turning over and thus the differentiation of the airway epithelium occurs in the presence of IL-13. Therefore, these models involve continuous stimulation of cultures during the 16-21-day (5-day exposure) or 11-21 day (10-day exposure) culture period when cells are actively undergoing mucociliary differentiation.

Using the optimized culture methods and media to propagate the ALI cultures, the use of the two types of IL-13 exposure models illustrated above have been implemented. Qualitative visual microscopic observations across all of the donors indicate that the 10-day treatment of cultures with IL-13 results in increased mucus production and decreased levels of ciliary movement compared to 5-day treatment with IL-13. Furthermore, each respective IL-13 treatment resulted in higher levels of mucus production and lower levels of cilia movement compared to their respective control treated cultures. The conditioned media secretome samples were then collected from each of the donors listed above and the proteins and metabolites that are unique and specific to IL-13-stimulated samples were identified as described below.

E. Further Optimization of IL-13 Treatment

Although the initial optimized results indicated that overall BSA levels were dramatically reduced compared to the first non-optimized experiment, a significant amount of BSA in the IL-13 but not mock-stimulated cultures (Table 3) was still observed. Further investigation into this phenomenon led the inventors to determine that the IL-13 cytokine used for these stimulations in the trial experiment was constituted and lyophilized by the manufacturer in bovine serum albumin (HSA)-containing buffer. Furthermore, reconstitution by the recipient user is suggested to be in a 0.1% BSA-containing buffer. To determine if the cytokine preparation itself was the source of the contaminating BSA identified in the samples. 250 ng of conventional IL-13 and carrier free (CF)-IL13 were dried down, trypsin digested, and analyzed on the mass spectrometer in the same manner as that used for the secretotne samples. It was found that the conventional IL-13 and its storage buffer are clearly the source of contaminating BSA in the IL-13 stimulated sample with nearly 50× times more BSA found within the conventional IL-13 sample compared to the carrier free sample.

TABLE 3

Proteins differentially expressed in the secretome of IL-13 Stimulated airway epithelial cells grown in ALI culture in AM2 media

| Protein | Detection and Quantitation | Donor 1 Control | Donor 1 IL13 | Donor 2 Control | Donor 2 IL13 | IL13 Secretome | Targeted RNA-seq Th2-high |
|---|---|---|---|---|---|---|---|
| IL-13 | Peptides detected | 0 | 3 | 0 | 1 | Up | Up |
|  | Intensity | 0 | 2.20E+05 | 0 | 5.75E+04 |  |  |
| Cytochrome P450 | Peptides detected | 0 | 1 | 0 | 1 | Up | — |
|  | Intensity | 0 | 1.3E+07 | 0 | 1.09E+07 |  |  |
| Periostin | Peptides detected | 0 | 13 | 0 | 2 | Up | Up |
|  | Intensity | 0 | 6.69E+04 | 0 | 1.37E+04 |  |  |
| Complement C3 | Peptides detected | 10 | 2 | 15 | 4 | Down | Down |
|  | Intensity | 1.15E+05 | 3.04E+04 | 8.05E+04 | 3.98E+04 |  |  |
| Cathepsin D | Peptides detected | 5 | 1 | 2 | 0 | Down | — |
|  | Intensity | 1.09E+05 | 9.55E+03 | 8.30E+04 | 0 |  |  |
| Cathepsin B | Peptides detected | 7 | 0 | 7 | 2 | Down | — |
|  | Intensity | 4.08E+05 | 0 | 1.34E+05 | 5.01E+04 |  |  |
| Stromelysin-2 (MMP10) | Peptides detected | 16 | 3 | 10 | 1 | Down | — |
|  | Intensity | 3.21E+05 | 4.57E+04 | 9.00E+04 | 2.80E+04 |  |  |
| MMP9 | Peptides detected | 5 | 0 | 2 | 0 | Down | — |
|  | Intensity | 6.94E+04 | 0 | 3.03E+04 | 0 |  |  |
| BSA | Peptides detected | 0 | 10 | 0 | 10 | — | — |
|  | Intensity | 0 | 3.86E+06 | 0 | 3.78E+06 |  |  |

Figure 6:
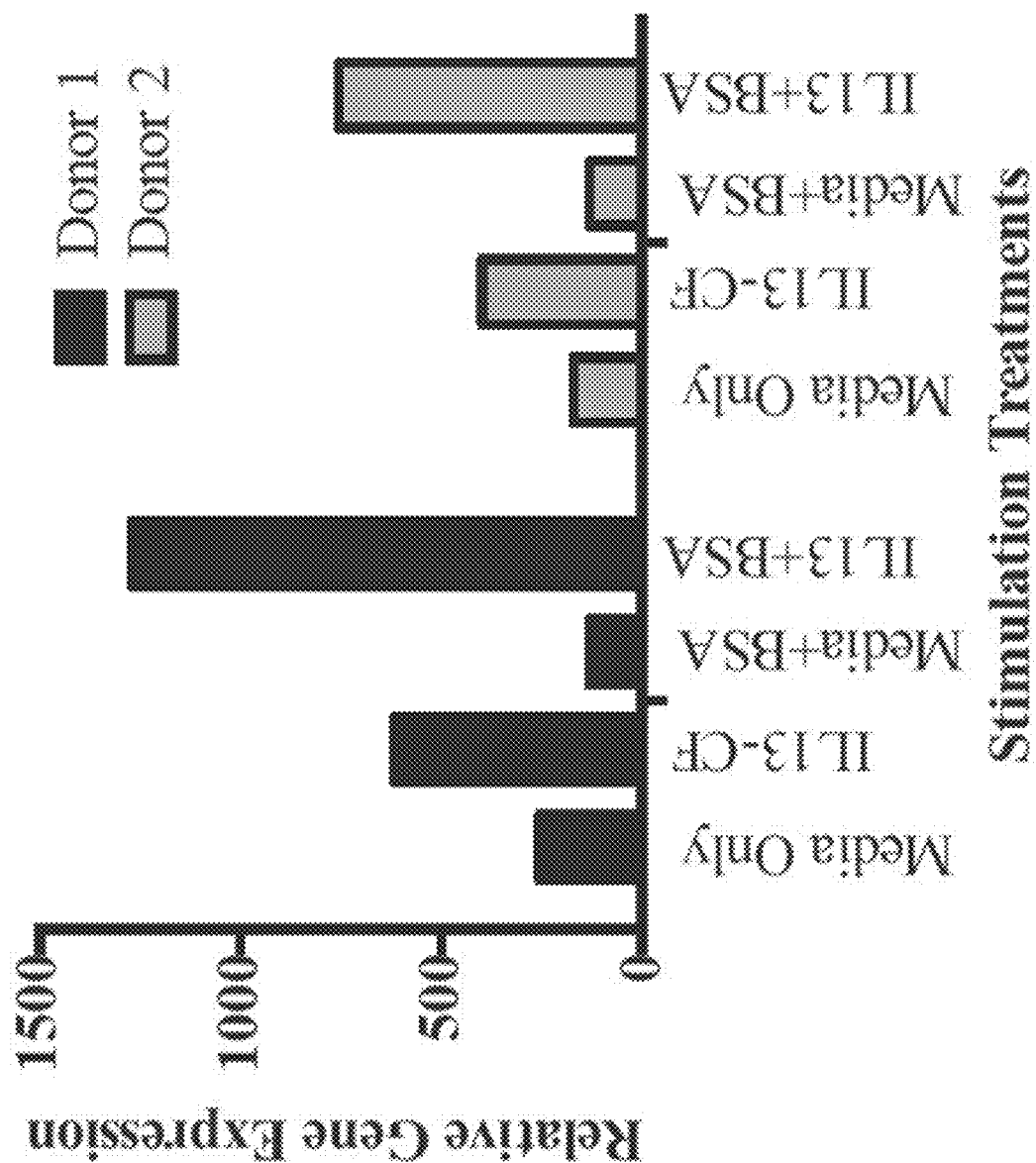
FIG. 6 shows expression of dipeptidyl peptidase 4 (DPP4) cultures stimulated for 5 days with IL-13/BSA followed by a 24 hour treatment with IL-13/BSA or carrier free IL-13.

Once it was determined that the IL-13 was the source of confounding BSA peptides, it was initially decided to utilize carrier-free IL-13 preparations to carry out the stimulations. Upon stimulation of cultures grown in the optimized PC-ALI media with carrier free IL-13, minimal periostin was identified in the mass spectrometry results. Longer stimulations were carried out for 5 days prior to media collection as described above. A trial was conducted to determine if there was a difference between the IL-13-induced responses in cells stimulated with conventional BSA-containing IL-13 and carrier free IL-13 during the last 24 hours of the stimulation timecourse. Gene expression of the IL-13-induced gene DPP4 demonstrates a distinct difference in cultures that differ only in the presence or absence of BSA within the IL-13 preparation (FIG. 6). It was determined that the carrier free IL-13 is much more readily lost in sticking to culture plastics and tubes, as well as more amenable to degradation at lower concentrations, and thus our stimulations with carrier-free IL-13 may not be at the concentration expected.

To successfully use the IL-13 containing carrier BSA for the stimulations, the evaluation of whether the addition of BSA to unstimulated control cultures would allow for optimal stimulation conditions while controlling for the additional bovine serum albumin in the mass spectrometry analysis. An equal concentration of BSA was spiked into unstimulated control wells over the same time course as IL-13 stimulation for 5 days and analyzed. As shown in FIG. 6, the effect of BSA on the expression of the IL-13 induced gene DPP4 was negligible compared to those without BSA. Mass spectrometry analysis identified nearly equal peptide counts of serum albumin peptides of bovine origin between the 2 samples. Additionally, the types of peptides, as well as their detected levels, were very close between samples stimulated with conventional IL-13 compared to carrier free IL-13 (Table 4).

TABLE 4

Proteins differentially expressed in the secretome of IL-13 stimulated airway epithelial cells grown in ALI culture in PC-ALI media
IL-13 Induced Secretome Proteins

| Protein | Detection and Quantitation | BSA Absent Media only | BSA Absent IL13 | BSA Present Media + BSA | BSA Present IL13 + BSA |
|---|---|---|---|---|---|
| Gelsolin | Peptide detected | 8 | 38 | 6 | 39 |
|  | Intensity | 1.49E+06 | 3.55E+07 | 1.12E+06 | 2.60E+07 |
| Intelectin-1 | Peptide detected | 0 | 6 | 0 | 5 |
|  | Intensity | 0.00E+00 | 2.60E+06 | 0.00E+00 | 1.13E+06 |

TABLE 4-continued

Proteins differentially expressed in the secretome of IL-13 stimulated airway epithelial cells grown in ALI culture in PC-ALI media
IL-13 Induced Secretome Proteins

| Protein | Detection and Quantitation | BSA Absent | | BSA Present | |
|---|---|---|---|---|---|
| | | Media only | IL13 | Media + BSA | IL13 + BSA |
| IgF CR-binding protein | Peptide detected | 0 | 16 | 0 | 5 |
| | Intensity | 0.00E+00 | 5.30E+06 | 0.00E+00 | 8.55E+05 |
| Plasminogen activator inhibitor 2 | Peptide detected | 0 | 9 | 1 | 7 |
| | Intensity | 0.00E+00 | 1.57E+06 | 3.20E+04 | 9.37E+05 |
| Selenimun-binding protein 1 | Peptide detected | 1 | 5 | 0 | 4 |
| | Intensity | 5.01E+04 | 8.19E+05 | 0.00E+00 | 2.31E+05 |
| Lysozyme C | Peptide detected | 0 | 5 | 0 | 6 |
| | Intensity | 0.00E+00 | 3.62E+06 | 0.00E+00 | 2.40E+06 |
| Arachidonate 15-lipoxygenase | Peptide detected | 0 | 8 | 0 | 4 |
| | Intensity | 0.00E+00 | 1.25E+06 | 0.00E+00 | 2.93E+05 |
| Trefoil Factor 3 | Peptide detected | 0 | 4 | 0 | 3 |
| | Intensity | 0.00E+00 | 9.51E+05 | 0.00E+00 | 1.13E+06 |
| Syndecan-4 | Peptide detected | 1 | 4 | 1 | 2 |
| | Intensity | 2.83E+04 | 3.83E+05 | 9.25E+04 | 4.93E+05 |
| Dipeptidyl Peptidase 1 | Peptide detected | 0 | 6 | 0 | 2 |
| | Intensity | 0.00E+00 | 1.19E+06 | 0.00E+00 | 3.99E+05 |
| Heat Shock Protein HSP90 | Peptide detected | 26 | 17 | 21 | 7 |
| | Intensity | 1.03E+07 | 2.61E+06 | 4.50E+06 | 5.68E+05 |
| Alpha actinin 4 | Peptide detected | 20 | 10 | 16 | 0 |
| | Intensity | 2.72E+06 | 6.34E+05 | 1.91E+06 | 0.00E+00 |
| Prelamin AC | Peptide detected | 14 | 5 | 8 | 3 |
| | Intensity | 4.30E+06 | 8.65E+05 | 1.93E+06 | 3.90E+05 |
| Triosephosphate isomerase | Peptide detected | 22 | 15 | 22 | 9 |
| | Intensity | 1.08E+07 | 9.41E+06 | 5.63E+06 | 3.31E+06 |
| Peptidyl-prolyl cis-transisomerase | Peptide detected | 14 | 10 | 14 | 7 |
| | Intensity | 1.13E+07 | 5.40E+06 | 7.09E+06 | 2.30E+06 |
| Serpin B5 | Peptide detected | 12 | 2 | 11 | 2 |
| | Intensity | 3.33E+06 | 1.67E+05 | 2.11E+06 | 6.45E+04 |
| Chloride Intracellular Channel Protein 1 | Peptide detected | 7 | 2 | 4 | 0 |
| | Intensity | 1.64E+06 | 2.68E+05 | 5.19E+05 | 0.00E+00 |
| Cathepsin D | Peptide detected | 10 | 8 | 14 | 7 |
| | Intensity | 1.94E+06 | 9.68E+05 | 2.16E+06 | 7.14E+05 |
| Galectin-3 binding protein | Peptide detected | 5 | 1 | 4 | 0 |
| | Intensity | 6.34E+05 | 3.35E+04 | 3.96E+05 | 0.00E+00 |

This data show that stimulations with conventional IL-13 containing BSA provide a higher and more consistent level of stimulation at both the gene and protein level. The addition of BSA to the unstimulated wells controls for the presence of BSA within the IL-13 samples during mass spectrometry analysis. Furthermore, the presence of the BSA does not detract from the identified peptides within the samples. This optimized method of stimulation has allowed the most accurate spectrum of peptides produced in the secretome of IL-13 stimulated cells to be gathered from the ALI cultures, as described below.

F. Proteomic Analysis

For preliminary experimental development, the IL-13-induced secretome in bronchial epithelial cells was examined from 2 healthy donors using a 24- and 48-hour IL-13 stimulation (Table 2). It was empirically determined that the level of protein produced by a 6.5 mm ALI insert was more than sufficient to produce a detectable range of peptides on the mass spectrometer. Three volumes of ice-cold methanol was added to the collected conditioned medium in order to precipitate proteins for proteomic analysis, and the supernatant was dried and prepped for metabolomics analysis. The precipitated proteins were speed vacuum dried and then Trypsin digested to produce peptides for mass spectrometry analysis. The proteomic analysis revealed 70-150 peptides in the airway epithelial secretome of each individual donor. These peptides represented >200 unique human proteins as determined by identification using an existing protein database (SwissProt Human Database).

Importantly, the inventors found periostin, a well-described marker of Th2-high asthma, specifically in the IL-13 stimulated, but not mock-stimulated, cultures of both donors (Table 3). This result validates the inventors' technical design, since periostin is detectable in the blood of Th2-high asthmatics. Additionally, the inventors observed decreased levels of the complement C3 protein in the IL-13—as compared to the mock-stimulated cultures. The finding is congruent with the inventors' previous RNA-seq analysis of in viva airway epithelial brushings, which revealed C3 was also down-regulated in Th2-high asthmatics (Table 3). As described herein, it was further determined that the use of BSA vs. carrier-free Th-13 preparations used in optimal PC-ALI grown cultures resulted in very similar peptides being stimulated and identified in the secretome via mass spectrometry (Table 4).

In the course of these trials the inventors optimized steps to collect and process conditioned media fractions. Additionally, the protocol for normalizing protein concentration between samples was optimized. For data analysis, it has been determined that the normalization of peptide detection between samples and batched runs is best done by normalizing the peptide count values for a particular protein to the total number of peptides detected within that sample in order to obtain a more accurate comparison between treatments, timepoints, and donor samples.

G. Metabolomic analysis

Basolateral media collected from the same experiment detailed above in the proteomic analysis was used to perform small molecule analysis. It was first determined whether there was sufficient levels of small molecules present in the collected media for metabolomic analysis. Samples were extracted using an organic liquid-liquid extraction which resulted in two fractions an aqueous fraction and a lipid fraction. The lipid fraction was analyzed in both positive and negative ionization mode on a time-of-flight mass spectrometer. Spectral data was extracted using Mass Hunter software (Agilent) and resulted in 1592 metabolites detected across the 2 donor samples. Differential analysis was performed using $p \leq 0.05$ and fold change $\geq 1.2$.

In both the 24-hour stimulation data and the 48 hour stimulation experiment, there was distinct up- and down-regulation of multiple metabolites across both samples between the control and IL-13-stimulated samples. Both inter-donor analysis (2 donors; FIG. 4) and intra-donor analysis (each donor conducted in duplicate; data not shown) indicates that each donor sample responded with differential expression levels, resulting in 45 statistically significant metabolites ($p<0.05$) with fold change $>1.2$.

Of these metabolites, 36 were up-regulated following stimulation while 9 were down-regulated after stimulation, some of which have been reported in the literature in association with asthma or lung disease. For example, the sphingolipids Sphingomyelin (d18:1/22:0) and Galabiosylceramide (d 18:1/12:0) were detected. Previous studies have associated sphingolipid dysregulation with COPD and asthma susceptibility. Two triglycerides were identified as up-regulated following stimulation. Triglycerides have been reported in the literature to the elevated in asthmatics who wheeze. Phospholipids have also been associated with asthma and COPD and 2 phospholipids were detected, phosphatidic acids (PA) and a LysoPE(18:1), Use of the IL-13 Stimulation Exposure Models:

Using the optimized culture methods and IL-13 stimulation exposure models, 5-day and 10-day stimulations were conducted and small molecule/metabolite fractions from each of the 19 donors were collected and cultured. The data described below is representative of samples from 5- and 10-day stimulations from 4 different donors.

Samples were prepared as described above, which resulted in a lipid and an aqueous fraction. The lipid fraction was analyzed in positive ionization mode using a C18 column on an Agilent 6410 ESI-TOF. Lipid peaks were extracted using Agilent's Mass Hunter Profinder software version B.06.625 and analyzed using FDR <0.05 and fold change >2.0 parameters to determine differential expression and statistical significance. Within the 4 donors analyzed, a total of 1,956 individual metabolites were identified; a value which indicates the validity of the sample collection and preparation prior to mass spectrometry and analysis.

Differential expression analysis was performed using the parameters of FDR <0.05 and fold change >2.0, and it was found that there were 350 differentially regulated metabolites resulting from the 5-day IL-13 exposure trial, and nearly 450 differentially regulated metabolites from the 10-day IL-13 exposure model stimulation. Further analysis determined that there are 135 metabolites that are not only differentially regulated, but are common among all 4 groups of donors analyzed. Hierarchical clustering of 66 of the 135 metabolites common to all 4 groups of donors indicates that while there are compounds that decrease with IL-13 stimulation, there is a much larger array of metabolites that dramatically increase within the conditioned media in presence of IL-13 over the course of 5- and 10-day exposures (Table 5), Table 5 shows the results of the differential expression analysis discussed above, wherein "up" indicates upregulation of the metabolite and "down" indicates downregulation of the metabolite at either the 5-day or 10-day IL-13 exposure stimulation.

TABLE 5

Metabolites

| Metabolite | IL13 10 days | IL13 5 days |
| --- | --- | --- |
| 3,3',4,5'-Tetrahydroxy-trans-stilbene | Down | Up |
| GlcCer(d15:2(4E,6E)/20:0(20H)) | Down | Up |
| D-Glucosyldihydrosphingosine | Down | Up |
| PA(19:0/19:0) | Down | Up |
| 2alpha-(benzyloxy)-1alpha,25-dihydroxy-19-norvitamin D3 | Down | Down |
| Histidylproline diketopiperazine | Down | Down |
| 2,2-Dichloro-1,1-ethanediol | Down | Down |
| Diphenylmethyphosphine | Down | Down |
| Gamma-glutamyl-L-putrescine | Down | Down |
| MG(17:0/0:0/0:0)[rac] | Down | Down |
| Ceramide (d18:1/22:0) | Up | Down |
| N1-(2-Methoxy-4-methylbenzyl)-n2-(2-(pyridin-2-yl)ethyl)oxalamide | Down | Down |

TABLE 5-continued

Metabolites

| Metabolite | IL13 10 days | IL13 5 days |
|---|---|---|
| (1R,6R)-6-Hydroxy-2-succinylcyclohexa-2,4-diene-1-carboxylate | Down | Down |
| DG(15:1(9Z)/22:5(7Z,10Z,13Z,16Z,19Z)/0:0)[iso2] | Down | Down |
| 6'',6''-Dimethyl-3',4'-methylenedioxypyrano[2'',3'':7,8]flavone | Down | Down |
| Tyrosyl-Glutamine | Down | Down |
| Homoanserine | Down | Down |
| PE-Cer(d16:1(4E)/18:1(9Z)(2OH)) | Down | Down |
| 1-Methyl-1,3-cyclohexadiene | Down | Down |
| 3-Hydroxyisopentyl-CoA | Up | Up |
| Isorhamnetin 3-gentiobioside-7-glucoside | Up | Up |
| PG(P-16:0/16:1(9Z)) | Up | Up |
| TG(16:1(9Z)/22:5(7Z,10Z,13Z,16Z,19Z)/16:1(9Z)) | Up | Up |
| 13-Deoxydaunorubicin | Up | Up |
| LysoPE(0:0/20:3(11Z,14Z,17Z)) | Up | Up |
| Glu Ile His | Up | Up |
| Cloβsone butyrate | Up | Up |
| Bis(4'-chlorophenyl)acetate | Up | Up |
| 1-Hexacosene | Up | Up |
| Caffeic acid 3-sulfate | Up | Up |
| 6-beta-Hydroxy-mometasone furoate | Up | Up |
| Fructoselysine | Up | Up |
| Tyr Ser Asp | Up | Up |
| Pantothenic acid | Up | Up |
| Kaempferol 3-neohesperidoside-7-(2''-p-coumaryllaminaribioside) | Up | Up |
| Dibenz[a,c]anthracene | Up | Up |
| N,N'-Diacetylchitobiosyldiphosphodolichol | Up | Up |
| Tyr Ala Val | Up | Up |
| Neu5Acα2-8Neu5Acα2-8Neu5Acα2-3Galβ1-4Glcβ-Sp | Up | Up |
| Harringtonine | Up | Up |
| Mycothione | Up | Up |
| Nap-Nap-OH | Up | Up |
| 6-Farnesyl-3',4',5,7-tetrahydroxyflavanone | Up | Up |
| 5Z-Tetradecenal | Up | Up |
| Mulberrofuran T | Up | Up |
| Sarcoaldesterol A | Up | Up |
| TG(20:1(11Z)/16:1(9Z)/18:3(9Z,12Z,15Z)) | Up | Up |
| Propoxycaine | Up | Up |
| 18-bromo-8E,17E19Z-tricosatrien-4,6-diynoic acid | Up | Up |
| TG(18:3(9Z,12Z,15Z)/20:4(5Z,8Z,11Z,4Z)/18:3(9Z,12Z,15Z)) | Up | Up |
| TG(16:1(9Z)/16:1(9Z)/22:6(4Z,7Z,10Z,13Z,16Z,19Z)) | Up | Up |
| TG(20:3(5Z,8Z,11Z)/14:1(9Z)/20:3n6) | Up | Up |
| TG(18:0/20:5(5Z,8Z,11Z,14Z,17Z)/18:4(6Z,9Z,12Z,15Z)) | Up | Up |
| TG(20:2n6/16:1(9Z)/20:2n6) | Up | Up |
| Pyridoxal (Vitamin B6) | Up | Up |
| (23R)-1aplha,25-dihydroxy-22,23,23,24-tetradehydrovitamin D3 | Up | Up |
| Steviobioside | Up | Up |
| Euchrenone b1 | Up | Up |
| DG(18:2(9Z,12Z)/20:4(5Z,8Z,11Z,14Z)/0:0) | Up | Up |
| Arcaine | Up | Up |
| Lys-Lys-OH | Up | Up |
| Phe Ser Thr | Up | Up |
| Docosahexaenoyl Serotonin | Up | Up |
| Lycocemuine | Up | Up |
| Heptaphylline | Up | Up |
| Docosahexaenoyl Serotonin | Up | Up |

With a subset of metabolomics data analyzed, it is clear that there is a dramatic change in the metabolite fraction of the secretome in the presence of IL-13; specifically, in the levels of phospholipids and vitamins identified as dysregulated, H. Development of Targeted Plasma Assays for Detection of IL-13 Induced Peptides To test how well the results found using the in vitro ALI culture model and IL-13 exposure methods describe above, translate to Th2 status prediction, quantitative plasma assay(s) for IL-13-induced proteins identified in the proteomics portion of this study has been developed. Labeled peptides for 5 of the most up-regulated and biologically significant proteins identified in the proteomics results have been obtained.

Figure 7A:
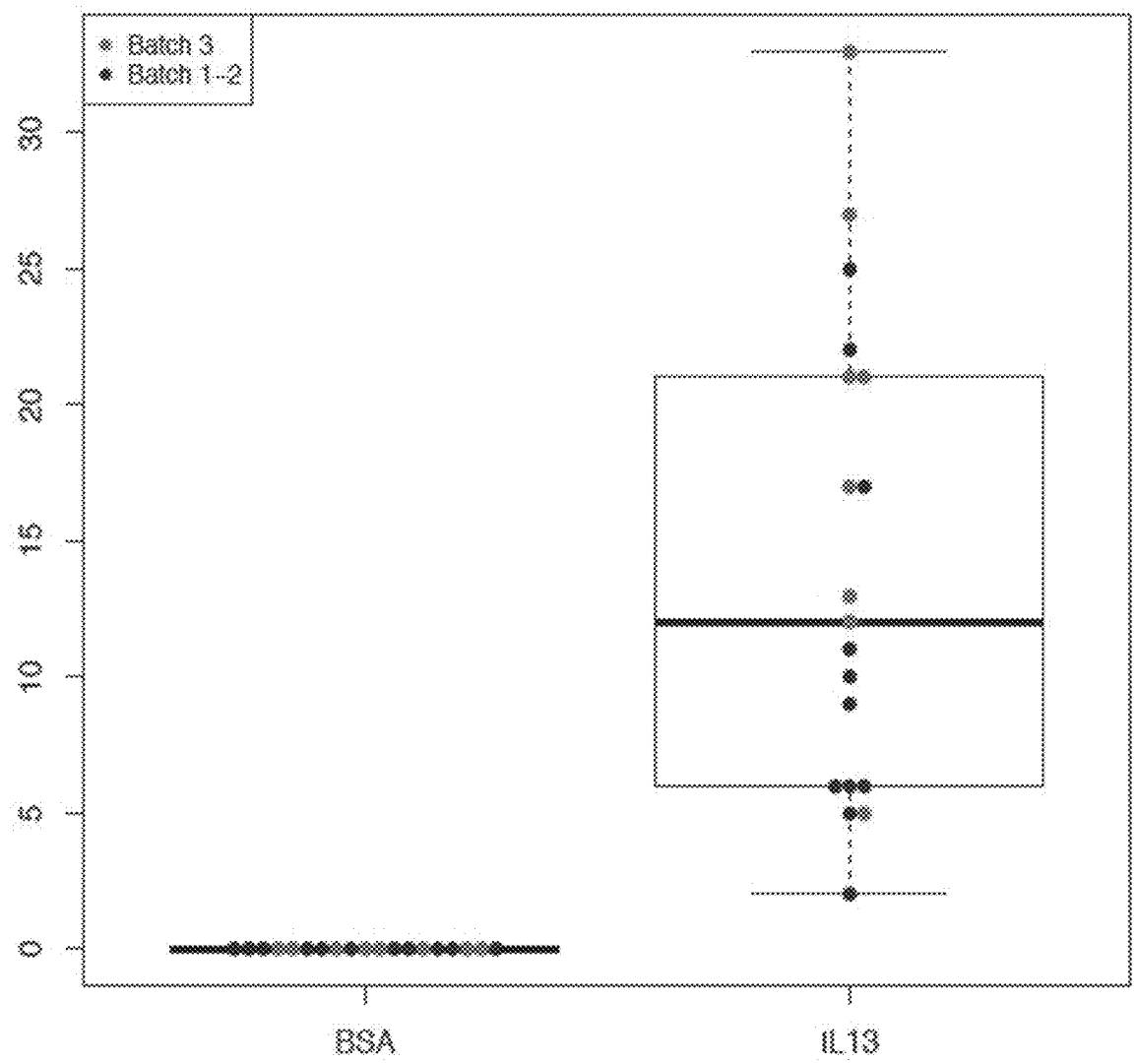
FIGS. 7A-7E shows Beeswann plots illustrating levels of detected peptides in control (bovine serum albumin (BSA)) treated and IL-13 treated (stimulated) samples. IL-13-induced protein biomarkers from a mass-spectrometer analysis in the presence or absence of IL-13 stimulation. In vitro ALI cultured bronchial epithelial cells were utilized for analyzing the basolateral secretome in response to IL-13 stimulation over the course of 10 days.
Figure 7B:
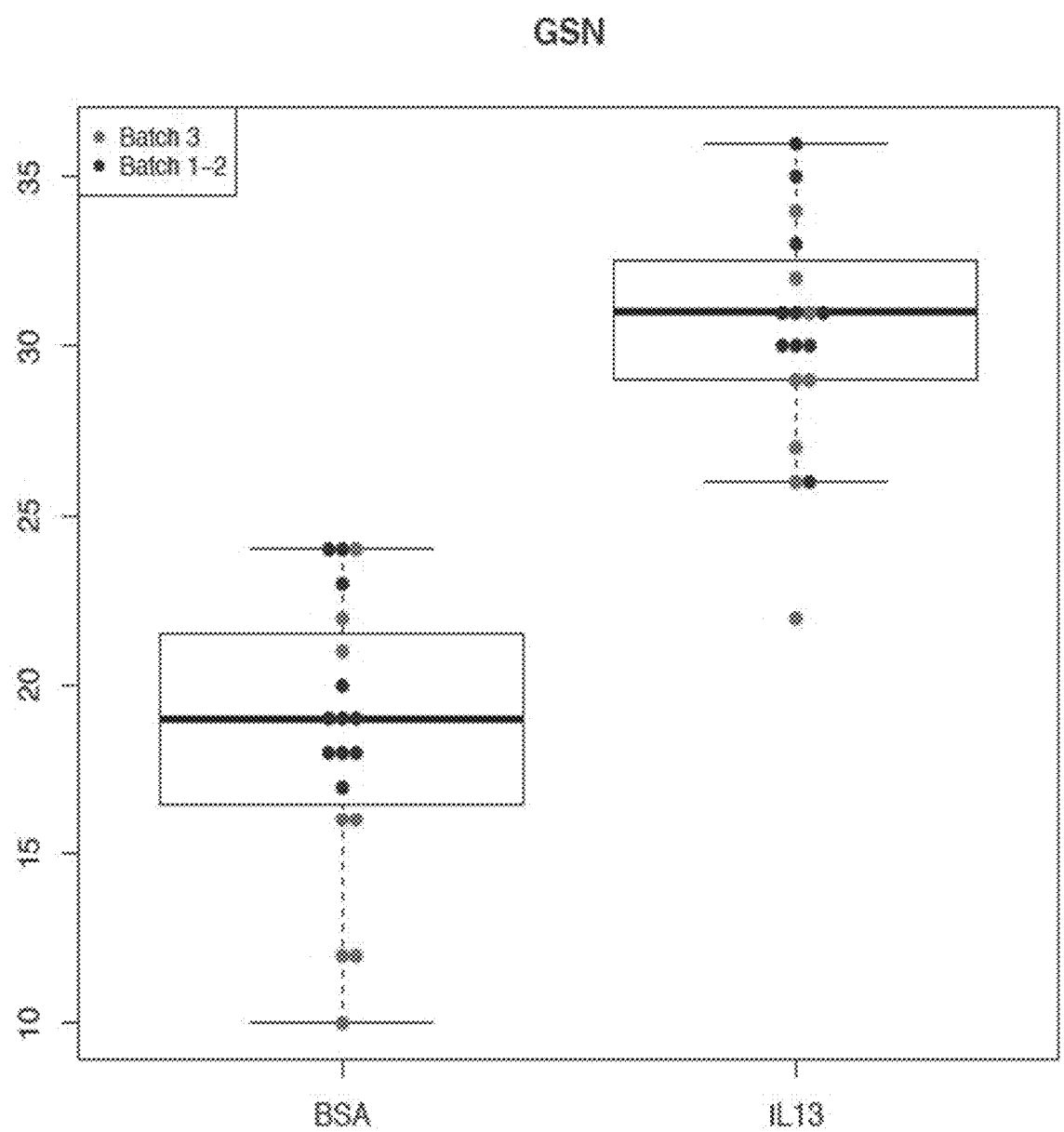
Figure 7C:
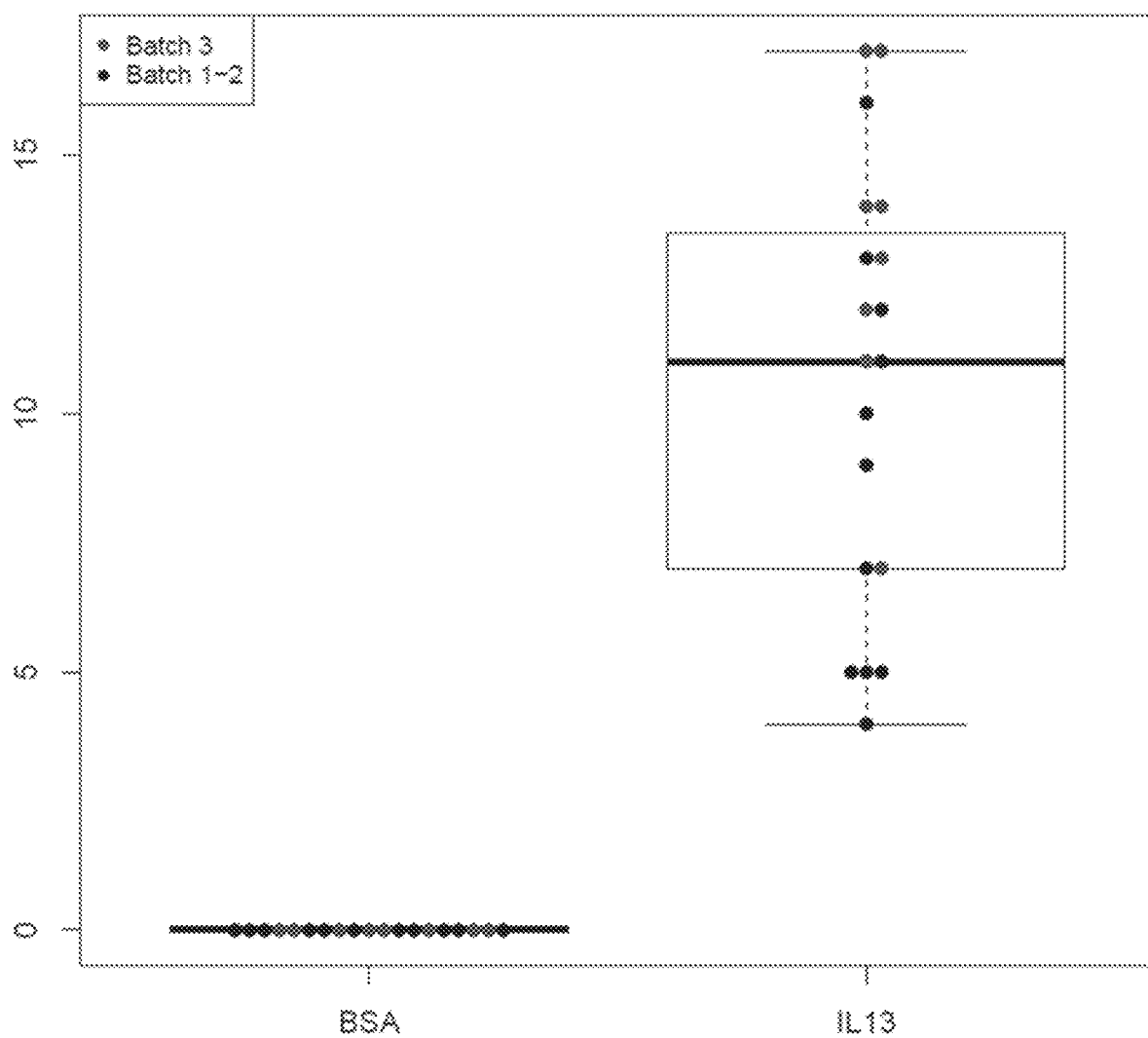
Figure 7D:
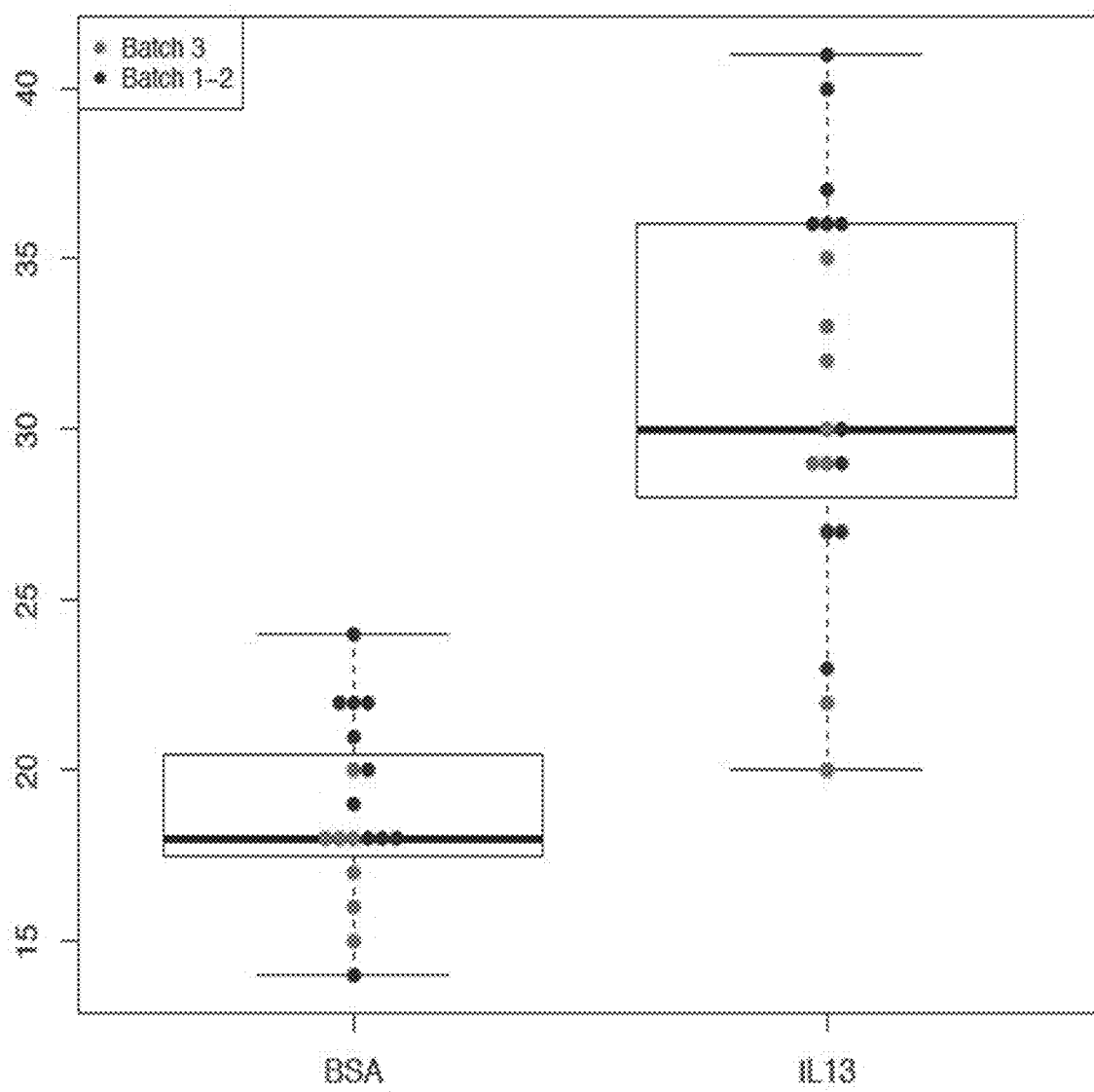
Figure 7E:
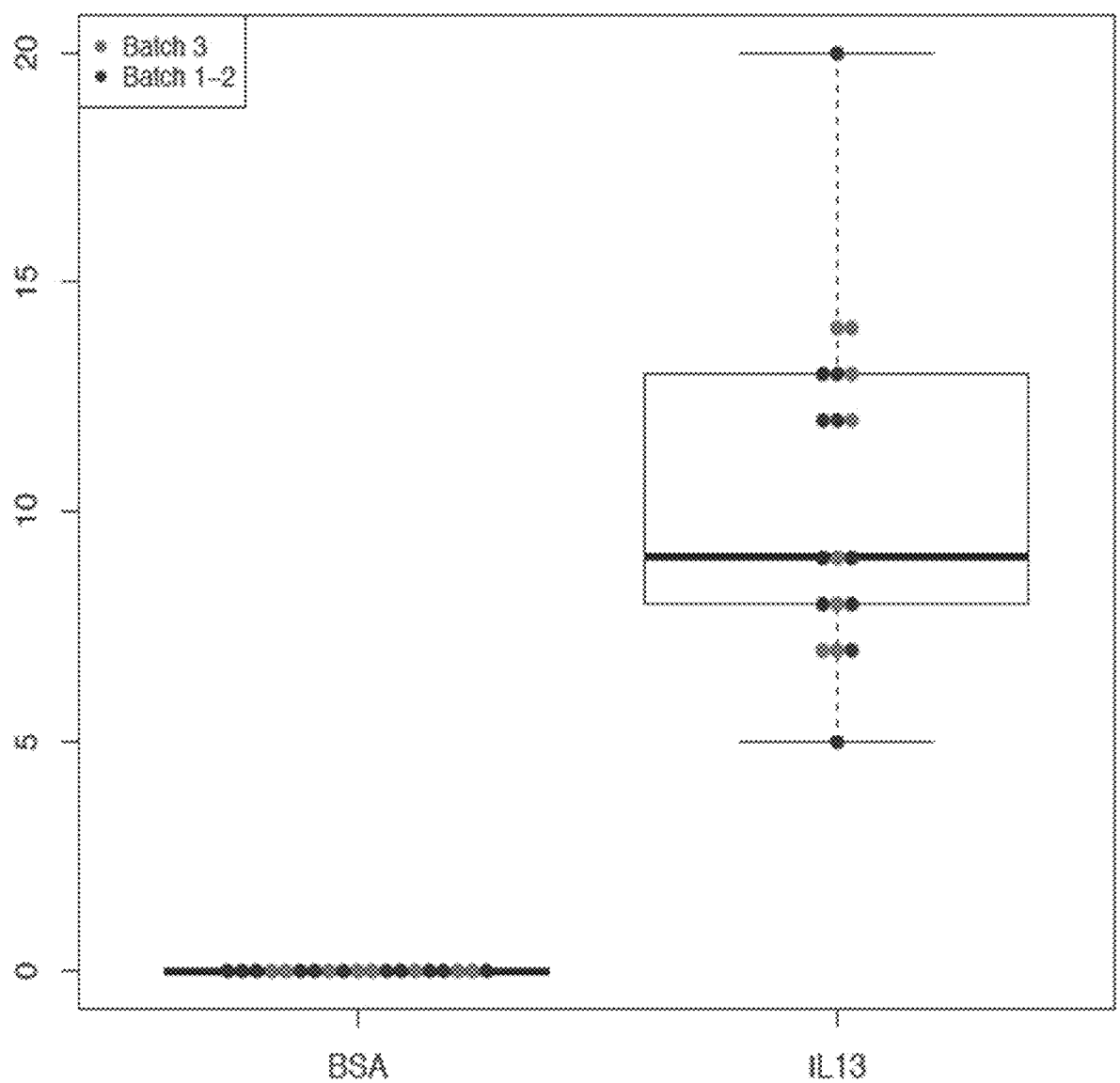
Figure 8A:
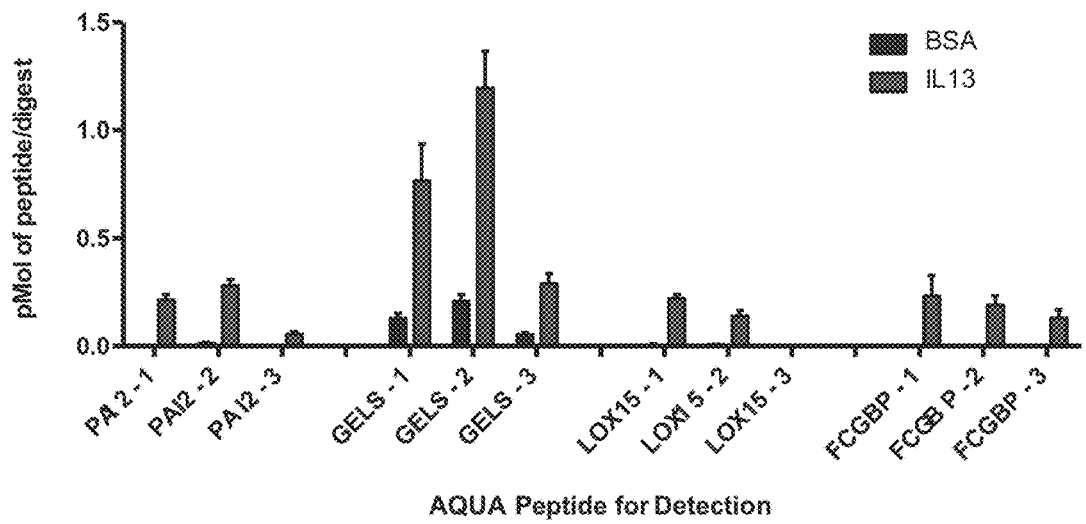
FIGS. 8A and 8B shows results from in vitro quantitative mass spectrometry blood assays for IL-13 induced proteins (FCGBP, ALOX15, SERPINB2, GELS and PIGR), wherein three distinct assays per protein are shown (indicated with −1, −2, or −3 following the protein name), providing for optimal sensitivity and specificity. AQUA peptide was used for detection. BSA, was used as a control and is represented in each bar graph grouping as the first bar. In many cases, no bar is seen for the BSA sample as the levels too low to show on graphs.
Figure 8B:
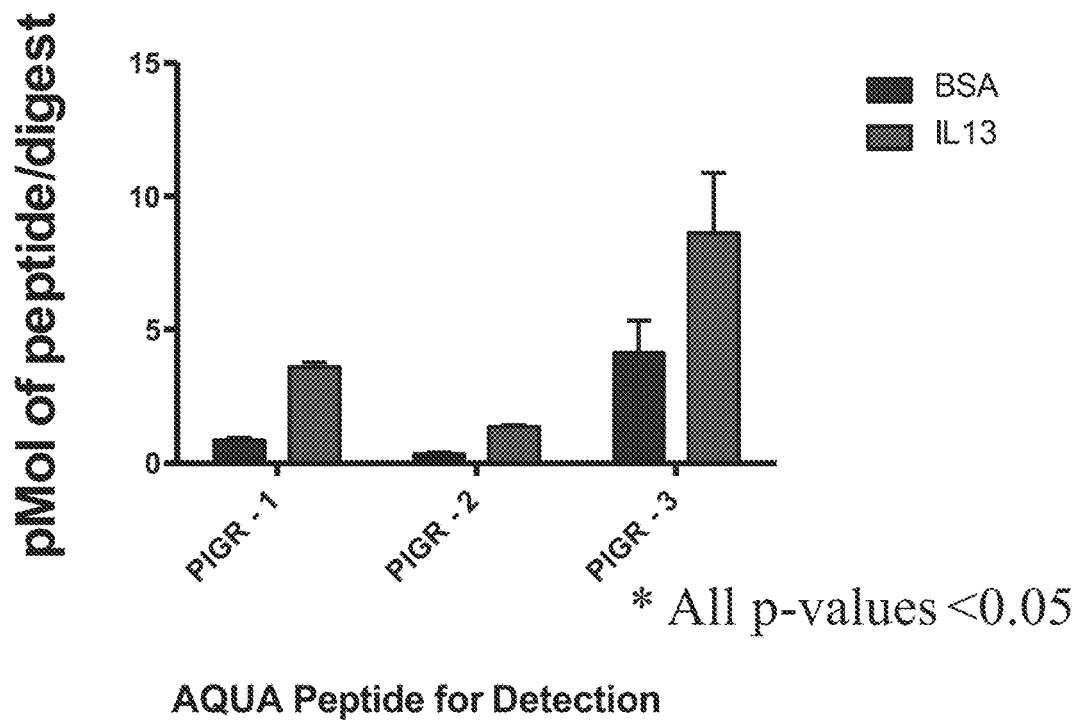

For these targeted assays, 2 of the most highly expressed proteins identified in the study: Gelsolin (GSN) and Polymeric Immunoglobulin Receptor (PIGR) (FIGS. 7B and 7D) have been chosen. While expressed and detected at low levels in control treated samples, IL-13 stimulation resulted in the highest upregulation of these 2 proteins among each of the donors tested and analyzed. In addition, 3 more proteins were chosen for the plasma assays Plasminogen Activator Inhibitor 2 (PAI2 also referred to as SERPINB2) (FIG. 7E), IgG-Fc Binding Protein (FCGBP) (FIG. 7A), and Arachidonic 15-lipoxygenase (ALOX15) (FIG. 7C). Each of these proteins is significantly upregulated in response to IL-13 treatment. Furthermore, each of these 3 chosen proteins is not detectable in control-treated donor cultures among each of the donors.

The ability to predict the Th2 status of asthmatic patients based on their circulating plasma proteins (noted above) can be done by using these targeted plasma assays.

Example 2 shows airway epithelial IL-13 secretome small molecules and proteins are detectable in the plasma of childhood asthmatics and that their levels can predict airway Th2-high asthma status.

Small molecules and proteins secreted basolaterally in response to IL-13 are predicted to enter the bloodstream and be detectable in patient plasma samples. Therefore both semi-quantitative and targeted analysis is preformed on the plasma from a cohort of 50 childhood asthmatics (already recruited) whose Th2-status can be determined by targeted RNA-seq of nasal brushings. Following semi-quantitative proteomics and metabolomics approaches to translate results from Example 1, quantitative mass spectrometry assays are used to measure in the plasma up to 10 small molecules or proteins that were the most highly and selectively secreted in response to IL-13 stimulation of airway epithelium.

I. Determining Th2 Status of Childhood Asthmatics

As part of the Gene Admixture in Latino Americans (GALA) cohort, nasal brushings and RNA from each respective brushing has been obtained, and paired blood samples from 100 childhood asthmatics. The inventors have previously demonstrated that stratification of patients based on Th2 status can be conducted based on the RNA expression profile of the nasal cells obtained from each donor. RNA-seq libraries can be constructed in order to determine the Th2 status of each donor within the cohort study in order to predict their Th2 status (if they have for example Th2-high asthma) using targeted detection of peptides described above in serum samples from each donor.

Example 3 shows that IL-13 induces a unique protein secretome from human airway epithelial cells that modulates mucus-related proteins and ciliary motion.

Gene expression analyses of bronchial airway brushings have found ~50% of asthmatics exhibit persistent type 2 cytokine-driven airway inflammation. These type 2-high asthmatics have an allergic phenotype with eosinophilia and high IgE levels. Importantly, type 2-high asthmatics have been identified as the responding group to inhaled corticosteroid treatment and are likely responders to type 2 cytokine inhibitors under development. Minimally invasive methods are needed to perform this endotyping clinically and in large research studies. To further study type 2 airway inflammation and reveal important extracellular effects of IL-13 stimulation, we evaluated the protein secretome, transcriptome, and cellular function of IL-13 stimulated airway epithelial cells.

Methods

Human airway epithelial cells were obtained from bronchial brushings of 19 donors and differentiated at air-liquid interface (ALI) for 21 days. Paired ALI cultures were mock-treated or IL-13-treated daily during the final 10 days of cellular differentiation. An unbiased proteomic screen of both apical washes and basolateral media was performed by LC-MS. RNA-seq and ciliary motion analyses were also performed.

Results

IL-13 alters the apically secreted levels of 19 proteins including many mucin/mucin-like proteins, and proteins involved in chemical modification, cross-linking, and secretion of mucins (e.g. intelectin 1 (ITLN1), 2,6-sialtransferase (SIAT1), and chloride channel accessory 1 (CLCA1)). This suggested shift in the mucus architecture during IL-13 stimulation is supported by ciliary motion analysis, which demonstrates that stimulation significantly decreases cilia beat frequency and increases the amplitude range of the ciliary stroke. This effect is observed only in complete cultures, and is abrogated upon removal of the mucus layer. RNA-seq gene expression levels and secreted protein detection are positively correlated (p 0.78) between most of the differentially expressed mnRNA-protein pairs. The basolateral IL-13 induced secretome was evaluated for possible blood-accessible airway type 2 inflammation biomarkers since these proteins would have access to the capillaries. 30 proteins were found at significantly higher levels in IL-13 stimulated basolateral media including 18 proteins exclusive to the IL-13 stimulation (FDR <0.01). Among these were known blood-based (periostin) and bronchial expressed (SERPINB2) proteins, as well as novel markers of type 2 airway inflammation.

Conclusions

IL-13 stimulation greatly alters the apical protein secretome of airway epithelium, notably modifying proteins involved in mucus formation. These changes to airway mucus inhibit ciliary motion suggesting type 2 inflammation can drive the development of pathologic mucus in type 2-high patients. These basolateral secretome results reveal multiple proteins that can function as strong blood-based biomarkers of type 2 airway inflammation.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Wu, R., Y. H. Zhao, and M. M. Chang, Growth and differentiation of conducting airway epithelial cells in culture. Eur Respir J, 1997. 10(10): p. 2398-403.
2. Chu, H. W., et al., CRISPR-Cas9-mediated gene knockout in primary human airway epithelial cells reveals a proinflammatory role MUC18. Gene Ther, 2015. 22(10): p. 822-9.
3. Karp, P. H., et al., An in vitro model of differentiated human airway epithelia. Methods for establishing primary cultures. Methods Mol Biol, 2002. 188: p. 115-37.
4. Pemberton, A. D., et al., A single-nucleotide polymorphism in intelectin 1 is associated with increased asthma risk. J Allergy Clin. Immunol, 2008. 122(5): p. 1033-4.
5. Cimerman, N., et al., Serum cystatin C, a potent inhibitor of cysteine proteinases, is elevated in asthmatic patients. Clin Chim Acta, 2000. 300(1-2): p. 83-95.
6. Choy, D. F., et al., Gene expression patterns of Th2 inflammation and intercellular communication in asthmatic airways. J Immunol, 2011. 186(3): p. 1861-9.

What is claimed is:

1. A method of identifying and treating a subject having or at risk of having a type-2 (Th2) high asthma, the method comprising:
   a. obtaining a blood sample from the subject;
   b. determining the level of one or more interleukin-13 (IL-13) induced proteins in the sample, wherein the one or more IL-13 induced proteins is selected from the group consisting of polymeric immunoglobulin receptor (PIGR), IgG Fc-receptor binding protein (FCGBP), and combinations thereof;

c. comparing the level of the one or more IL-13 induced proteins in the sample to a control sample wherein a higher level of the one or more IL-13 induced proteins as compared to the control sample identifies the subject as having or at risk of having Th2 high asthma; and d. treating the subject identified as having or at risk of having Th2 high asthma in step c with a Th2 pathway inhibitor, wherein the Th2 pathway inhibitor is fingolimid (FTY720).

2. The method of claim 1, wherein the level of the one more IL-13 induced proteins is determined by a method selected from the group consisting of mass spectrometry, Western Blotting, Elisa and PCR.

3. The method of claim 1, wherein the blood sample is a plasma sample.

4. The method of claim 1, wherein the subject identified as having Th2 high asthma is further administered an inhaled corticosteroid.

5. A method of diagnosing and treating Th2 high asthma in a subject, the method comprising:

a. obtaining a blood sample from the subject;

b. determining the level of one or more IL-13 induced proteins in the sample, wherein the one or more IL-13 induced proteins is selected from the group consisting of PIGR, FCGBP, and combinations thereof;

c. comparing the level of the one or more IL-13 induced proteins in the sample to a control sample, wherein a higher level of the one or more IL-13 induced proteins as compared to the control sample identifies the subject as having Th2 high asthma; and d. administering an effective amount of a Th2 pathway inhibitor, wherein the Th2 pathway inhibitor is fingolimid (FTY720).

6. The method of claim 5, wherein the level of the one more IL-13 induced proteins is determined by a method selected from the group consisting of mass spectrometry, Western Blotting, Elisa and PCR.

7. The method of claim 5, wherein the blood sample is a plasma sample.

8. A method to endotype a subject having Th2-high asthma and treating said subject, the method comprising:

a. obtaining a blood sample from the subject;

b. determining the level of one or more IL-13 induced proteins in the sample, wherein the one or more IL-13 induced proteins is selected from the group consisting of PIGR, FCGBP, and combinations thereof;

c. determining the level of the same one or more IL-13 induced proteins from step b in a control sample, and endotyping the subject as having Th2-high asthma when a higher level of the one or more IL-13 induced proteins as compared to the control sample is determined; and d. treating the subject endotyped as having Th2 high asthma in step c with fingolimid (FTY720).

9. A method to predict the response of a subject to treatment with a Th2 pathway inhibitor, who has Th2 high asthma, the method comprising a. obtaining a blood sample from the subject;

b. determining the level of one or more interleukin-13 (IL-13) induced proteins in the sample, wherein the one or more IL-13 induced proteins is selected from the group consisting of PIGR, FCGBP, and combinations thereof;

c. comparing the level of the one or more IL-13 induced proteins in the sample to a control sample wherein a higher level of the one or more IL-13 induced proteins as compared to the control sample predicts the subject is responsive to treatment with a Th2 pathway inhibitor; and d. treating the subject from step c with a Th2 pathway inhibitor wherein the Th2 pathway inhibitor is fingolimid (FTY720).

10. The method of claim 5, wherein the subject identified as having Th2 high asthma is further administered an inhaled corticosteroid.

11. The method of claim 8, wherein the subject identified as having Th2 high asthma is further administered an inhaled corticosteroid.

12. The method of claim 9, wherein the subject identified as having Th2 high asthma is further administered an inhaled corticosteroid.

* * * * *